US008377957B2

(12) United States Patent
Kshirsagar et al.

(10) Patent No.: US 8,377,957 B2
(45) Date of Patent: *Feb. 19, 2013

(54) HYDROXY AND ALKOXY SUBSTITUTED 1H-IMIDAZOQUINOLINES AND METHODS

(75) Inventors: Tushar A. Kshirsagar, Woodbury, MN (US); Philip D. Heppner, Forest Lake, MN (US); Scott E. Langer, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/306,366

(22) Filed: Nov. 29, 2011

(65) Prior Publication Data
US 2012/0071463 A1 Mar. 22, 2012

Related U.S. Application Data

(63) Continuation of application No. 12/092,625, filed as application No. PCT/US2006/042905 on Nov. 3, 2006, now Pat. No. 8,088,790.

(60) Provisional application No. 60/733,952, filed on Nov. 4, 2005.

(51) Int. Cl.
*C07D 471/04* (2006.01)
*A61K 31/541* (2006.01)
*A61K 31/5377* (2006.01)
*A61K 31/496* (2006.01)
*A61K 31/4745* (2006.01)

(52) U.S. Cl. ............... 514/293; 514/232.8; 514/253.03; 514/217.07; 514/228.5; 514/218; 514/215; 544/126; 544/361; 544/60; 540/597; 540/575; 540/585; 546/82

(58) Field of Classification Search ............... 514/293, 514/232.8, 253.03, 217.07, 228.5, 218, 215; 544/126, 361, 60; 540/597, 575, 585; 546/82
See application file for complete search history.

(56) References Cited

U.S. PATENT DOCUMENTS

| 3,314,941 A | 4/1967 | Littell et al. | |
| 4,689,338 A | 8/1987 | Gerster | 514/293 |
| 4,698,348 A | 10/1987 | Gerster | |
| 4,929,624 A | 5/1990 | Gerster et al. | |
| 4,988,815 A | 1/1991 | Andre et al. | 546/159 |
| 5,037,986 A | 8/1991 | Gerster | |
| 5,175,296 A | 12/1992 | Gerster | |
| 5,238,944 A | 8/1993 | Wick et al. | |
| 5,266,575 A | 11/1993 | Gerster | |
| 5,268,376 A | 12/1993 | Gerster | 514/293 |
| 5,346,905 A | 9/1994 | Gerster | |
| 5,352,784 A | 10/1994 | Nikolaides et al. | 594/126 |
| 5,367,076 A | 11/1994 | Gerster | |
| 5,389,640 A | 2/1995 | Gerster et al. | 514/293 |
| 5,395,937 A | 3/1995 | Nikolaides et al. | 546/82 |
| 5,444,065 A | 8/1995 | Nikolaides et al. | |
| 5,446,153 A | 8/1995 | Lindstrom et al. | |
| 5,482,936 A | 1/1996 | Lindstrom | |
| 5,494,916 A | 2/1996 | Lindstrom et al. | |
| 5,525,612 A | 6/1996 | Gerster | |
| 5,627,281 A | 5/1997 | Nikolaides et al. | |
| 5,644,063 A | 7/1997 | Lindstrom et al. | |
| 5,648,516 A | 7/1997 | Nikolaides et al. | |
| 5,693,811 A | 12/1997 | Lindstrom | |
| 5,714,608 A | 2/1998 | Gerster | |
| 5,741,908 A | 4/1998 | Gerster et al. | |
| 5,756,747 A | 5/1998 | Gerster | 546/82 |
| 5,886,006 A | 3/1999 | Nikolaides et al. | |
| 5,939,090 A | 8/1999 | Beaurline et al. | |
| 6,039,969 A | 3/2000 | Tomai et al. | |
| 6,069,149 A | 5/2000 | Nanba et al. | 514/293 |
| 6,083,505 A | 7/2000 | Miller et al. | |
| 6,110,929 A | 8/2000 | Gerster et al. | |
| 6,194,425 B1 | 2/2001 | Gerster et al. | |
| 6,200,592 B1 | 3/2001 | Tomai et al. | |
| 6,245,776 B1 | 6/2001 | Skwierczynski et al. | 514/293 |
| 6,331,539 B1 | 12/2001 | Crooks et al. | 514/228.5 |
| 6,365,166 B2 | 4/2002 | Beaurline et al. | |
| 6,376,669 B1 | 4/2002 | Rice et al. | |
| 6,440,992 B1 | 8/2002 | Gerster et al. | |
| 6,451,810 B1 | 9/2002 | Coleman et al. | 514/293 |
| 6,486,168 B1 | 11/2002 | Skwierczynski et al. | |
| 6,514,985 B1 | 2/2003 | Gerster et al. | |
| 6,518,265 B1 | 2/2003 | Kato et al. | 514/228.5 |
| 6,525,064 B1 | 2/2003 | Dellaria et al. | |
| 6,541,485 B1 | 4/2003 | Crooks et al. | 514/293 |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |

(Continued)

FOREIGN PATENT DOCUMENTS

EP 0 394 026 10/1990
EP 1 104 764 6/2001

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

(Continued)

*Primary Examiner* — Joseph Kosack
*Assistant Examiner* — Matthew Coughlin

(57) ABSTRACT

1H-Imidazo[4,5-c]quinolin-4-amines with a hydroxy, alkoxy, hydroxyalkoxy, or alkoxyalkoxy substituent at the 2-position, pharmaceutical compositions containing these compounds, methods of making the compounds, intermediates, and methods of use of these compounds as immunomodulators, for inducing cytokine biosynthesis in animals and in the treatment of diseases including viral and neoplastic diseases, are disclosed.

22 Claims, No Drawings

U.S. PATENT DOCUMENTS

| | | |
|---|---|---|
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. ............ 514/232.8 |
| 6,660,735 B2 | 12/2003 | Crooks et al. |
| 6,660,747 B2 | 12/2003 | Crooks et al. ................ 514/293 |
| 6,664,260 B2 | 12/2003 | Charles et al. ................ 514/256 |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. ................ 514/293 |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stroermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 8,088,790 B2 * | 1/2012 | Kshirsagar et al. ........... 514/293 |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. ..................... 514/44 |
| 2003/0185835 A1 | 10/2003 | Braun ........................ 424/184.1 |
| 2004/0014779 A1 | 1/2004 | Gorden et al. |
| 2004/0076633 A1 | 4/2004 | Thomsen et al. .......... 424/184.1 |
| 2004/0132079 A1 | 7/2004 | Gupta et al. |
| 2004/0147543 A1 | 7/2004 | Hays et al. ..................... 514/292 |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. ......... 424/178.1 |
| 2004/0265351 A1 | 12/2004 | Miller et al. .................. 424/423 |
| 2005/0009858 A1 | 1/2005 | Martinez-Colon et al. ... 514/292 |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. ............... 546/82 |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |
| 2007/0208052 A1 | 9/2007 | Prince et al. |
| 2007/0213355 A1 | 9/2007 | Capraro et al. |
| 2007/0213356 A1 | 9/2007 | Merrill et al. |
| 2007/0219196 A1 | 9/2007 | Krepski et al. |
| 2007/0243215 A1 | 10/2007 | Miller et al. |

| | | |
|---|---|---|
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188469 A1 | 8/2008 | Thomsen et al. .......... 514/229.8 |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0275077 A1 | 11/2008 | Skwierczynski et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. ......... 514/227.8 |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2005/0239735 A1 | 10/2010 | Miller et al. |

FOREIGN PATENT DOCUMENTS

| | | |
|---|---|---|
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Higuchi, T., et al., "Pro-drugs as Novel Delivery Systems", A.C.S. Symposium Series, vol. 14. 1974.

Koller, G., (Kohler, "sic") "Uber eine Synthese des 2.4-Dioxychinolin-3-carbonsaure-methylesters", Berichte der deutschen chemischen Gesellschaft (A and B Series), 1927, pp. 1108-1113, Issue a5, vol. 60.

Buckle, D., et al., "4-Hydroxy-3-nitro-2-quinolones and related compounds as inhibitors of allergic reactions", J. Medicinal Chemistry, Aug. 1975, pp. 726-732, Issue 7, vol. 18.

Kappe, Thomas, et al., "Synthesis of Benzo-halogenated 4-Hydroxy-2(1H)-quinolones", J. Heterocyclic Chemistry, May-Jun. 1988, pp. 857-862, vol. 25.

Testerman, et al., "Cyctokine Induction by the Immunomodulators Imiquimod and S-27609", Journal of Leukocyte Biology, Sep. 1995, pp. 365-372, 58.

Gerster et al "Synthesis and Structure-Activity-Relationships of 1H-Imidazo[4,5-c]quinolines That Induce Interferon Production" J Med. Chem. 2005, 48, pp. 3481-3491. ISBN: 9788391327951.

\* cited by examiner

HYDROXY AND ALKOXY SUBSTITUTED 1H-IMIDAZOQUINOLINES AND METHODS

CROSS REFERENCE TO RELATED APPLICATIONS

This application a continuation of U.S. patent application Ser. No. 12/092,625, file Jan. 8, 2009 now U.S. Pat. No. 8,088,790, which is the National Stage filing under 35 U.S.C. 371 of International Application No. PCT/US2006/042905, filed Nov. 3, 2006, which claims the benefit of U.S. Provisional Application No. 60/733,952, filed Nov. 4, 2005, which is incorporated herein by reference in its entirety.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY OF THE INVENTION

It has now been found that certain 2-hydroxy- and 2-alkoxy-1H-imidazo[4,5-c]quinolin-4-amines modulate cytokine biosynthesis. In one aspect, the present invention provides compounds, which are of the following Formulas I, II, and III:

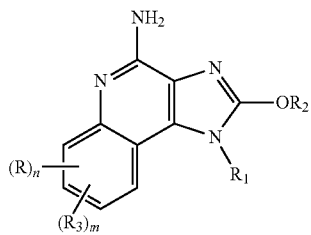

I

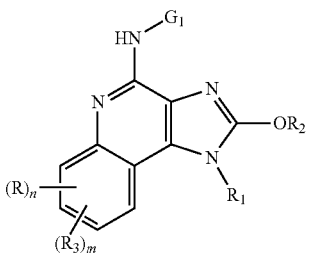

II

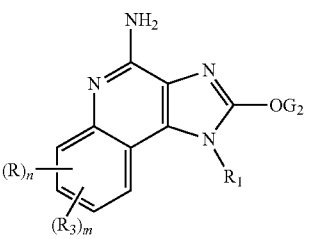

III wherein R, $R_1$, $R_2$, $R_3$, $G_1$, $G_2$, n, and m are as defined below; and pharmaceutically acceptable salts thereof.

The compounds or salts of Formulas I, II, and III are useful as IRMs due to their ability to modulate cytokine biosynthesis (e.g., induce the biosynthesis or production of one or more cytokines) and otherwise modulate the immune response when administered to animals. In some embodiments, compounds or salts of Formula I can be especially useful as immune response modifiers due to their ability to selectively induce interferon (α) (IFN-α), thus providing a benefit over compounds that also induce pro-inflammatory cytokines (e.g. TNF-α) or that induce pro-inflammatory cytokines at higher levels. The ability to modulate cytokine biosynthesis makes the compounds useful in the treatment of a variety of conditions such as viral diseases and neoplastic diseases that are responsive to such changes in the immune response.

In another aspect, the present invention also provides pharmaceutical compositions containing the compounds of Formulas I, II, and/or III.

In another aspect of particular importance, the present invention provides methods of inducing cytokine biosynthesis in animal cells, selectively inducing IFN-α in animal cells, treating a viral disease in an animal, and/or treating a neoplastic disease in an animal by administering to the animal one or more compounds of the Formulas I, II, and/or III, and/or pharmaceutically acceptable salts thereof.

In another aspect, the invention provides methods of synthesizing the compounds of Formulas I, II, and III and intermediate compounds useful in the synthesis of these compounds.

As used herein, "a", "an", "the", "at least one", and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I, II, and III:

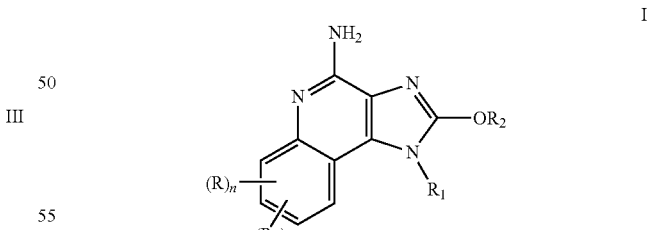

I

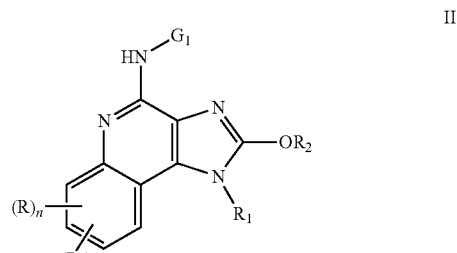

II

-continued

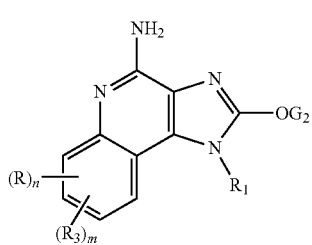

III wherein R, $R_1$, $R_2$, $R_3$, $G_1$, $G_2$, n, and m are as defined below; and pharmaceutically acceptable salts thereof.

In one embodiment, the present invention provides a compound of the following Formula I:

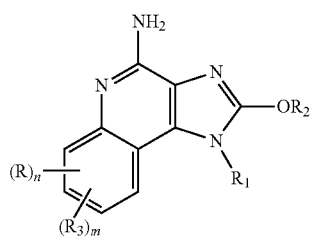

I wherein:
$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;
R is selected from the group consisting of:
halogen,
hydroxy,
alkyl,
alkenyl,
haloalkyl,
alkoxy,
alkylthio, and
—N($R_9$)$_2$;
n is an integer from 0 to 4;
$R_1$ is selected from the group consisting of:
hydrogen,
—CH($R_{11}$)—Ar,
—CH($R_{11}$)—Ar'—$R_4$,
—CH($R_{11}$)—Ar'—Y—$R_4$,
—CH($R_{11}$)—Ar'—CH($R_{11}$)—Y—$R_4$,
—CH($R_{11}$)—Ar'—$R_5$,
—CH($R_{11}$)—Ar'—CH($R_{11}$)—$R_5$,
—$X_1$-Het, and
—$X_1$—N($R_8$)-Q-$R_4$;
Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;
Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;
Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;
$X_1$ is $C_{1-6}$ alkylene that is optionally interrupted by one or more —O— groups;
$R_{11}$ is selected from the group consisting of hydrogen and $C_{1-3}$ alkylene;
$R_3$ is selected from the group consisting of:
—Z—$R_4$,
—Z—X—$R_4$,
—Z—X—Y—$R_4$,
—Z—X—Y—X—Y—$R_4$, and
—Z—X—$R_5$;
m is 0 or 1; with the proviso that when m is 1, then n is 0 or 1;
X is selected from the group consisting of alkylene, alkenylene, alkynylene, arylene, heteroarylene, and heterocylylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

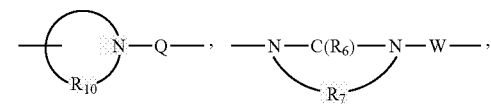

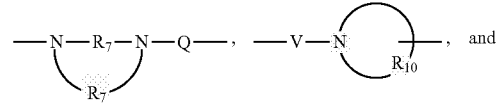, and

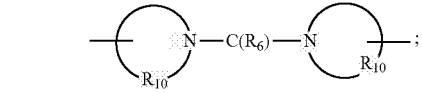;

Z is a bond or —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy;

heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

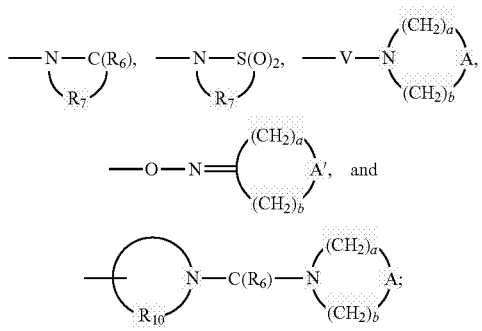

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, the present invention provides a compound of the following Formula II, which is a prodrug:

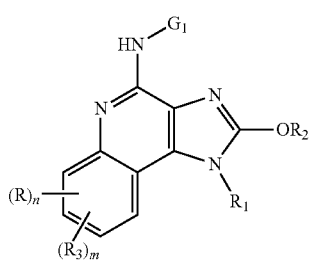

II wherein:
$G_1$ is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(OC$_{1-4}$ alkyl)Y$_0$,
—CH$_2$Y$_1$, and
—CH(CH$_3$)Y$_1$;
R' and R" are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;
α-aminoacyl is an α-aminoacyl group derived from an amino acid selected from the group consisting of racemic, D-, and L-amino acids;
Y' is selected from the group consisting of hydrogen, $C_{1-6}$ alkyl, and benzyl;
$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl;
$Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;
$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;
R is selected from the group consisting of:
halogen,
hydroxy,
alkyl,
alkenyl,
haloalkyl,
alkoxy,
alkylthio, and
—N(R$_9$)$_2$;
n is an integer from 0 to 4;
$R_1$ is selected from the group consisting of:
hydrogen,
—CH(R$_{11}$)—Ar,
—CH(R$_{11}$)—Ar'—R$_4$,
—CH(R$_{11}$)—Ar'—Y—R$_4$,
—CH(R$_{11}$)—Ar'—CH(R$_{11}$)—Y—R$_4$,
—CH(R$_{11}$)—Ar'—R$_5$,
—CH(R$_{11}$)—Ar'—CH(R$_{11}$)—R$_5$,
—X$_1$-Het, and
—X$_1$—N(R$_8$)-Q-R$_4$;
Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;
Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;
Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;
$X_1$ is $C_{1-6}$ alkylene that is optionally interrupted by one or more —O— groups;
$R_{11}$ is selected from the group consisting of hydrogen and $C_{1-3}$ alkylene;

$R_3$ is selected from the group consisting of:
—Z—$R_4$,
—Z—X—$R_4$,
—Z—X—Y—$R_4$,
Z—X—Y—X—Y—$R_4$, and
—Z—X—$R_5$;

m is 0 or 1; with the proviso that when m is 1, then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

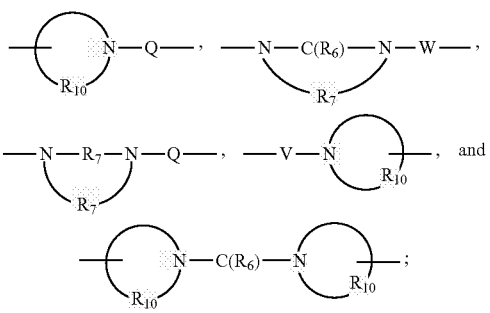

and

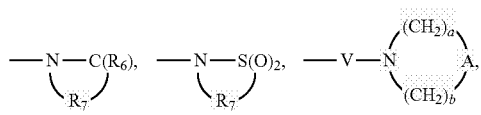

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

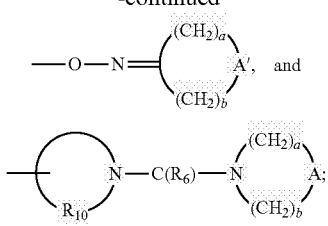

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

In another embodiment, the present invention provides a compound of the following Formula III, which is a prodrug:

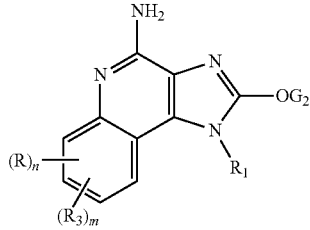

III wherein:
$G_2$ is selected from the group consisting of:
—$X_2$—C(O)—R',
α-aminoacyl,
α-aminoacyl-α-aminoacyl,
—$X_2$—C(O)—O—R',
—C(O)—N(R")R', and
—S(O)$_2$—R;
$X_2$ is selected from the group consisting of a bond; —CH$_2$—O—; —CH(CH$_3$)—O—; —C(CH$_3$)$_2$—O—; and, in the case of —$X_2$—C(O)—O—R', —CH$_2$—NH—;
R' and R" are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an amino acid selected from the group consisting of racemic, D-, and L-amino acids;

R is selected from the group consisting of:
halogen,
hydroxy,
alkyl,
alkenyl,
haloalkyl,
alkoxy,
alkylthio, and
—N(R$_9$)$_2$;

n is an integer from 0 to 4;

R$_1$ is selected from the group consisting of:
hydrogen,
—CH(R$_{11}$)—Ar,
—CH(R$_{11}$)—Ar'—R$_4$,
—CH(R$_{11}$)—Ar'—Y—R$_4$,
—CH(R$_{11}$)—Ar'—CH(R$_{11}$)—Y—R$_4$,
—CH(R$_{11}$)—Ar'—R$_5$,
—CH(R$_{11}$)—Ar'—CH(R$_{11}$)—R$_5$,
—X$_1$-Het, and
—X$_1$—N(R$_8$)-Q-R$_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

X$_1$ is C$_{1-6}$ alkylene that is optionally interrupted by one or more —O— groups;

R$_{11}$ is selected from the group consisting of hydrogen and C$_{1-3}$ alkylene;

R$_3$ is selected from the group consisting of:
—Z—R$_4$,
—Z—X—R$_4$,
—Z—X—Y—R$_4$,
Z—X—Y—X—Y—R$_4$, and
—Z—X—R$_5$;

m is 0 or 1; with the proviso that when m is 1, then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—, —O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

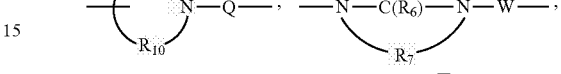

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of:

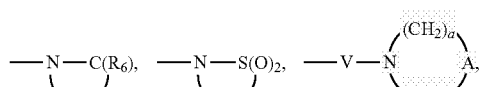

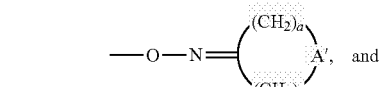

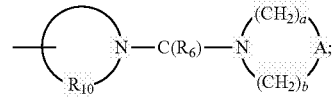

R$_6$ is selected from the group consisting of =O and =S;
R$_7$ is C$_{2-7}$ alkylene;
R$_8$ is selected from the group consisting of hydrogen, C$_{1-10}$ alkyl, C$_{2-10}$ alkenyl, hydroxy-C$_{1-10}$ alkylenyl, C$_{1-10}$ alkoxy-C$_{1-10}$ alkylenyl, aryl-C$_{1-10}$ alkylenyl, and heteroaryl-C$_{1-10}$ alkylenyl;
R$_9$ is selected from the group consisting of hydrogen and alkyl;
R$_{10}$ is C$_{3-8}$ alkylene;

A is selected from the group consisting of —CH$_2$—, —O—, —C(O)—, —S(O)$_{0-2}$—, and —N(-Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is $\leq 7$;

or a pharmaceutically acceptable salt thereof.

For any of the compounds presented herein, each one of the following variables (e.g., R$_1$, R$_2$, G$_1$, G$_2$, R$_4$, R$_{11}$, X, X$_1$, Y, Y$_1$, A, Q, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, e.g., of Formula II, G$_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$. For certain of these embodiments, R' and R" are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an amino acid selected from the group consisting of racemic, D-, and L-amino acids;

Y' is selected from the group consisting of hydrogen, C$_{1-6}$ alkyl, and benzyl;

Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula II, G$_1$ is selected from the group consisting of —C(O)—R', α-aminoacyl, and —C(O)—O—R'.

For certain embodiments, including any one of the above embodiments of Formula II, G$_1$ is selected from the group consisting of —C(O)—R', α-amino-C$_{2-11}$ acyl, and —C(O)—O—R'. α-Amino-C$_{2-11}$ acyl includes α-amino acids containing a total of at least 2 carbon atoms and a total of up to 11 carbon atoms, and may also include one or more heteroatoms selected from the group consisting of O, S, and N.

For certain embodiments, e.g., of Formula III, G$_2$ is selected from the group consisting of —X$_2$—C(O)—R', α-aminoacyl, α-aminoacyl-α-aminoacyl, —X$_2$—C(O)—O—R', —C(O)—N(R")R', and —S(O)$_2$—R'. For certain of these embodiments, X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—;

R' and R" are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and α-aminoacyl is an α-aminoacyl group derived from an amino acid selected from the group consisting of racemic, D-, and L-amino acids.

For certain embodiments, including any one of the above embodiments which include an α-aminoacyl group, α-aminoacyl is an α-aminoacyl group derived from a naturally occurring amino acid selected from the group consisting of racemic, D-, and L-amino acids.

For certain embodiments, including any one of the above embodiments which include an α-aminoacyl group, α-aminoacyl is an α-aminoacyl group derived from an amino acid found in proteins, wherein the amino acid is selected from the group consisting of racemic, D-, and L-amino acids.

For certain embodiments, including any one of the above embodiments of Formula III, G$_2$ is selected from the group consisting of α-amino-C$_{2-5}$ alkanoyl, C$_{2-6}$ alkanoyl, C$_{1-6}$ alkoxycarbonyl, and C$_{1-6}$ alkylcarbamoyl.

For certain embodiments, the R$_2$ group of Formula II is replaced by G$_2$, wherein G$_2$ is defined as in any one of the above embodiments containing G$_2$.

For certain embodiments, including any one of the above embodiments of Formula I, II, or III, R$_1$ is selected from the group consisting of hydrogen, —CH(R$_{11}$)—Ar, —CH(R$_{11}$)—Ar'—R$_4$, —CH(R$_{11}$)—Ar'—Y—R$_4$, —CH(R$_{11}$)—Ar'—CH(R$_{11}$)—Y—R$_4$, —CH(R$_{11}$)—Ar'—R$_5$, —CH(R$_{11}$)—Ar'—CH(R$_{11}$)—R$_5$, —X$_1$-Het, and X$_1$—N(R$_8$)-Q-R$_4$.

For certain embodiments, including any one of the above embodiments of Formula I, II, or III, R$_1$ is —CH(R$_{11}$)—Ar. For certain of these embodiments, R$_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen. For certain of these embodiments, R$_1$ is selected from the group consisting of benzyl, 4-methoxybenzyl, 1-phenylethyl, and pyridin-3-ylmethyl.

For certain embodiments, including any one of the above embodiments of Formula I, II, or III, R$_1$ is —CH(R$_{11}$)—Ar'—CH(R$_{11}$)—Y—R$_4$, except where R$_1$ is —CH(R$_{11}$)—Ar. For certain of these embodiments, each R$_{11}$ is hydrogen; Ar' is phenylene;

Y in —CH(R$_{11}$)—Ar'—CH(R$_{11}$)—Y—R$_4$ is —NHQwherein Q is selected from the group consisting of —C(O)—, —S(O)$_2$—, —C(R$_6$)—N(R$_8$)—, —S(O)$_2$—N(R$_8$)—, —C(O)—O—, and —C(O)—S—; and R$_4$ in —CH(R$_{11}$)—Ar'—CH(R$_{11}$)—Y—R$_4$ is selected from the group consisting of alkyl, aryl, heteroaryl, and arylalkylenyl wherein alkyl, aryl, and heteroaryl are each unsubstituted or substituted by one or more substituents independently selected from the group consisting of alkyl, alkoxy, and halogen.

For certain embodiments, including any one of the above embodiments of Formula I, II, or III, $R_1$ is —CH($R_{11}$)—Ar'—CH($R_{11}$)—$R_5$, except where $R_1$ is —CH($R_{11}$)—Ar or —CH($R_{11}$)—Ar'—CH($R_{11}$)—Y—$R_4$. For certain of these embodiments, each $R_{11}$ is hydrogen; Ar' is phenylene; and $R_5$ in —CH($R_{11}$)—Ar'—CH($R_{11}$)—$R_5$ is

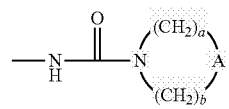

wherein A is selected from the group consisting of —CH$_2$—, —O—, and —N(alkyl)-, and a and b are each independently 1, 2, or 3.

For certain embodiments, including any one of the above embodiments of Formula I, II, or III, $R_1$ is —$X_1$—N($R_8$)-Q-$R_4$, except where $R_1$ is —CH($R_{11}$)—Ar, —CH($R_{11}$)—Ar'—CH($R_{11}$)—Y—$R_4$, or —CH($R_{11}$)—Ar'—CH($R_{11}$)—$R_5$. For certain of these embodiments, $X_1$ is $C_{1-4}$ alkylene; $R_8$ in —$X_1$—N($R_8$)-Q-$R_4$ is hydrogen; Q in —$X_1$—N($R_8$)-Q-$R_4$ is selected from the group consisting of —C(O)—, —S(O)$_2$—, —C($R_6$)—N($R_8$)—, and —S(O)$_2$—N($R_8$)—; and $R_4$ in —$X_1$—N($R_8$)-Q-$R_4$ is selected from the group consisting of alkyl, aryl, heteroaryl, heterocyclyl, and arylalkylenyl wherein alkyl, aryl, and heteroaryl are each unsubstituted or substituted by one or more substituents independently selected from the group consisting of alkyl, alkoxy, and halogen. Alternatively, for certain of these embodiments, $X_1$ is $C_{1-4}$ alkylene; $R_8$ in —$X_1$—N($R_8$)-Q-$R_4$ is $C_{1-10}$ alkyl or hydroxy-$C_{1-10}$ alkylenyl; Q in —$X_1$—N($R_8$)-Q-$R_4$ is a bond; and $R_4$ in —$X_1$—N($R_8$)-Q-$R_4$ is selected from the group consisting of alkyl, aryl, arylalkylenyl, and heteroarylalkylenyl wherein alkyl is optionally substituted by one or more substituents independently selected from the group consisting of alkoxy and hydroxy.

For certain embodiments, including any one of the above embodiments of Formula I, II, or III, $R_1$ is —$X_1$-Het, except where $R_1$ is —CH($R_{11}$)—Ar, —CH($R_{11}$)—Ar'—CH($R_{11}$)—Y—$R_4$, —CH($R_{11}$)—Ar'—CH($R_{11}$)—$R_5$, or —$X_1$—N($R_8$)-Q-$R_4$. For certain of these embodiments Het is selected from the group consisting of piperidinyl, piperazinyl, morpholinyl, thiomorpholinyl, azepanyl, and dihydroisoquinolin-(1H)-yl each of which is optionally substituted by one or more substituents independently selected from the group consisting of alkyl and hydroxy.

For certain embodiments, including any one of the above embodiments of Formula I, II, or III, wherein $R_1$ can be —$X_1$-Het, $R_1$ is tetrahydropyranylmethyl. For certain of these embodiments, $R_1$ is tetrahydro-2H-pyran-4-ylmethyl.

For certain embodiments, including any one of the above embodiments of Formula I or II, $R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl.

For certain embodiments, including any one of the above embodiments of Formula I or II, $R_2$ is hydrogen.

For certain embodiments, including any one of the above embodiments of Formula I or II, $R_2$ is ethyl or propyl, except where $R_2$ is hydrogen.

For certain embodiments, including any one of the above embodiments of Formula I or II, $R_2$ is ethyl or propyl, and $R_1$ is hydrogen, except where $R_2$ is hydrogen or where $R_1$ is —CH($R_{11}$)—Ar, —CH($R_{11}$)—Ar'—CH($R_{11}$)—Y—$R_4$, —CH($R_{11}$)—Ar'—CH($R_{11}$)—$R_5$, —$X_1$—N($R_8$)-Q-$R_4$, or —$X_1$-Het.

For certain embodiments, including any one of the above embodiments of Formula I, II, or III, $R_3$ is selected from the group consisting of —Z—$R_4$, —Z—X—$R_4$, —Z—X—Y—$R_4$, Z—X—Y—X—Y—$R_4$, and —Z—X—$R_5$.

For certain embodiments, including any one of the above embodiments of Formula I, II, or III, $R_3$ is pyridin-3-yl, 3-hydroxyphenyl, 4-hydroxymethylphenyl, or benzyloxy. For certain of these embodiments, n is 0.

For certain embodiments, including any one of the above embodiments of Formula I, II, or III, $R_3$ is at the 7-position. For certain of these embodiments, n is 0.

For certain embodiments, including any one of the above embodiments of Formula I, II, or III, R is selected from the group consisting of halogen, hydroxy, alkyl, alkenyl, haloalkyl, alkoxy, alkylthio, and —N($R_9$)$_2$.

For certain embodiments, including any one of the above embodiments of Formula I, II, or III, R is hydroxy. For certain of these embodiments n is 1. For certain of these embodiments, m is 0.

For certain embodiments, including any one of the above embodiments of Formula I, II, or III, m and n are both 0, except where this definition for m and n is excluded.

In one embodiment, the present invention provides a compound selected from the group consisting of 4-amino-1-benzyl-1H-imidazo[4,5-c]quinolin-2-ol, 4-amino-1-(1-phenylethyl)-1H-imidazo[4,5-c]quinolin-2-ol, 4-amino-1-(4-methoxybenzyl)-1H-imidazo[4,5-c]quinolin-2-ol, and 4-amino-1-(pyridin-3-ylmethyl)-1H-imidazo[4,5-c]quinolin-2-ol, or a pharmaceutically acceptable salt thereof.

In another embodiment, the present invention provides the compound 4-amino-1-(tetrahydro-2H-pyran-4-ylmethyl)-1H-imidazo[4,5-c]quinolin-2-ol or a pharmaceutically acceptable salt thereof.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo.

For certain embodiments, $R_4$ is selected from the group consisting of alkyl, aryl, heteroaryl, and arylalkylenyl wherein alkyl, aryl, and heteroaryl are each unsubstituted or substituted by one or more substituents independently selected from the group consisting of alkyl, alkoxy, and halogen.

For certain embodiments, $R_4$ is selected from the group consisting of alkyl, aryl, heteroaryl, heterocyclyl, and arylalkylenyl wherein alkyl, aryl, and heteroaryl are each unsubstituted or substituted by one or more substituents independently selected from the group consisting of alkyl, alkoxy, and halogen.

For certain embodiments, $R_4$ is selected from the group consisting of alkyl, aryl, arylalkylenyl, and heteroarylalkylenyl wherein alkyl is optionally substituted by one or more substituents independently selected from the group consisting of alkoxy and hydroxy.

For certain embodiments, $R_5$ is selected from the group consisting of:

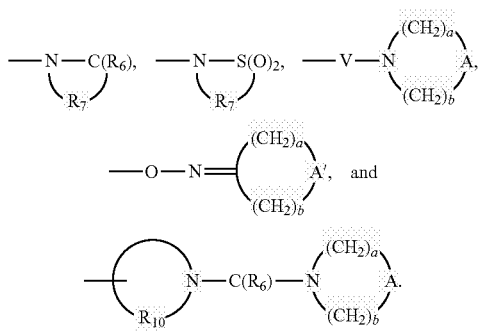

For certain embodiments, $R_5$ is

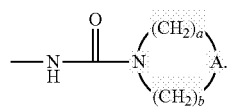

For certain embodiments, $R_6$ is selected from the group consisting of =O and =S.

For certain embodiments, $R_6$ is =O.

For certain embodiments, $R_6$ is =S.

For certain embodiments, $R_7$ is $C_{2-7}$ alkylene.

For certain embodiments, $R_7$ is $C_{2-4}$ alkylene.

For certain embodiments, $R_7$ is ethylene.

For certain embodiments, $R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl.

For certain embodiments, $R_8$ is hydrogen, $C_{1-10}$ alkyl, or hydroxy-$C_{1-10}$ alkylenyl.

For certain embodiments, $R_8$ is $C_{1-10}$ alkyl or hydroxy-$C_{1-10}$ alkylenyl.

For certain embodiments, $R_8$ is hydrogen.

For certain embodiments, $R_9$ is selected from the group consisting of hydrogen and alkyl.

For certain embodiments, $R_{10}$ is $C_{3-8}$ alkylene.

For certain embodiments, $R_{10}$ is pentylene.

For certain embodiments, $R_H$ is selected from the group consisting of hydrogen and $C_{1-3}$ alkylene.

For certain embodiments, $R_H$ is methyl.

For certain embodiments, $R_H$ is hydrogen.

For certain embodiments, R' is selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, R" is selected from the group consisting of hydrogen, $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, A is selected from the group consisting of —$CH_2$—, —O—, —C(O)—, —$S(O)_{0-2}$—, and —N(-Q-$R_4$)—.

For certain embodiments, A is selected from the group consisting of —$CH_2$—, —O—, and —N(alkyl)-.

For certain embodiments, A is —O—.

For certain embodiments, A' is selected from the group consisting of —O—, —$S(O)_{0-2}$—, —N(-Q-$R_4$)—, and —$CH_2$—.

For certain embodiments, Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino.

For certain embodiments, Ar is phenyl.

For certain embodiments, Ar is pyridinyl.

For certain embodiments, Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino.

For certain embodiments, Ar' is phenylene.

For certain embodiments, Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo.

For certain embodiments, Het is heterocyclyl which is unsubstituted or substituted by one or more substituents independently selected from the group consisting of alkyl, alkoxy, haloalkyl, haloalkoxy, halogen, nitro, hydroxy, cyano, amino, alkylamino, dialkylamino, and oxo.

For certain embodiments, Het is selected from the group consisting of piperidinyl, piperazinyl, morpholinyl, thiomorpholinyl, azepanyl, and dihydroisoquinolin-(1H)-yl each of which is optionally substituted by one or more substituents independently selected from the group consisting of alkyl and hydroxy.

For certain embodiments, Het is tetrahydropyranyl.

For certain embodiments, Het is tetrahydro-2H-pyran-4-yl.

For certain embodiments, Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, —$C(R_6)$—S—, and —$C(R_6)$—$N(OR_9)$—.

For certain embodiments, Q is selected from the group consisting of —C(O)—, —$S(O)_2$—, —$C(R_6)$—$N(R_8)$—, —$S(O)_2$—$N(R_8)$—, —C(O)—O—, and —C(O)—S—.

For certain embodiments, Q is —C(O)—, —$S(O)_2$—, —$C(R_6)$—$N(R_8)$—, and —$S(O)_2$—$N(R_8)$—.

For certain embodiments, Q is —$C(R_6)$—.

For certain embodiments, Q is a bond.

For certain embodiments, V is selected from the group consisting of —$C(R_6)$—, —O—$C(R_6)$—, —$N(R_8)$—$C(R_6)$—, and —$S(O)_2$—.

For certain embodiments, V is —$N(R_8)$—C(O)—.

For certain embodiments, W is selected from the group consisting of a bond, —C(O)—, and —$S(O)_2$—.

For certain embodiments, W is a bond.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X is $C_{1-4}$ alkylene.

For certain embodiments, X is methylene.

For certain embodiments, $X_1$ is $C_{1-6}$ alkylene that is optionally interrupted by one or more —O— groups.

For certain embodiments, $X_1$ is $C_{1-4}$ alkylene

For certain embodiments, $X_2$ is selected from the group consisting of a bond; —$CH_2$—O—; —$CH(CH_3)$—O—; —$C(CH_3)_2$—O—; and, in the case of —$X_2$—C(O)—O—R', —$CH_2$—NH—.

For certain embodiments, Y is selected from the group consisting of —O—, —$S(O)_{0-2}$—, —$S(O)_2$—$N(R_8)$—, —$C(R_6)$—, —$C(R_6)$—O—, —O—$C(R_6)$—, —O—C(O)—O—, —$N(R_8)$-Q-, —$C(R_6)$—$N(R_8)$—, —O—$C(R_6)$—$N(R_8)$—, —$C(R_6)$—$N(OR_9)$—, —O—$N(R_8)$-Q-, —O—N=$C(R_4)$—, —C(=N—O—$R_8$)—, —CH(—N(—O—$R_8$)-Q-$R_4$)—,

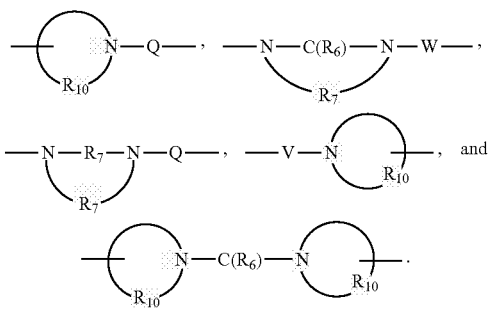

For certain embodiments, Y is —$N(R_8)$-Q-.

For certain embodiments, Y is selected from the group consisting of —$N(R_8)$—C(O)—, —$N(R_8)$—$S(O)_2$—, —$N(R_8)$—$C(R_6)$—$N(R_8)$—, —$N(R_8)$—$S(O)_2$—$N(R_8)$—, —$N(R_8)$—$C(R_6)$—O—, and —$N(R_8)$—$C(R_6)$—S—.

For certain embodiments, Y is —NHQ-.

For certain embodiments, Y is selected from the group consisting of —N(H)—C(O)—, —N(H)—$S(O)_2$—, —N(H)—$C(R_6)$—$N(R_8)$—, —N(H)—$S(O)_2$—$N(R_8)$—, —N(H)—C(O)—O—, and —N(H)—C(O)—S—.

For certain embodiments, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl.

For certain embodiments, Y' is selected from the group consisting of hydrogen, $C_{1-6}$ alkyl, and benzyl.

For certain embodiments, Z is a bond or —O—.

For certain embodiments, Z is a bond.

For certain embodiments, Z is —O—.

For certain embodiments, a and b are independently integers from 1 to 6 with the proviso that a+b is $\leq 7$. For certain embodiments, a and b are each independently 1, 2, or 3. For certain embodiments, a and b are each 2.

For certain embodiments, m is 0 or 1; with the proviso that when m is 1, then n is 0 or 1.

For certain embodiments, m is 1, and n is 0 or 1.

For certain embodiments, m is 1, and n is 0.

For certain embodiments, m is 0.

For certain embodiments, n is an integer from 0 to 4.

For certain embodiments, n is 1.

For certain embodiments, n is 0.

For certain embodiments, m is 0, and n is 0.

For certain embodiments, the present invention provides a pharmaceutical composition comprising a therapeutically effective amount of a compound or salt of any one of the above embodiments of Formulas I, II, and III, and a pharmaceutically acceptable carrier.

For certain embodiments, the present invention provides a method of inducing cytokine biosynthesis in an animal comprising administering an effective amount of a compound or salt of any one of the above embodiments of Formulas I, II, and III, or a pharmaceutical composition comprising an effective amount of a compound or salt of any one of the above embodiments of Formulas I, II, and III to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

For certain embodiments, the present invention provides a method of selectively inducing the biosynthesis of IFN-α in an animal comprising administering an effective amount of a compound or salt of any one of the above embodiments of Formulas I, II, and III, or a pharmaceutical composition comprising an effective amount of a compound or salt of any one of the above embodiments of Formulas I, II, and III to the animal.

For certain embodiments, the present invention provides a method of treating a viral disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III to the animal.

For certain embodiments, the present invention provides a method of treating a viral disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III the animal; and selectively inducing the biosynthesis of IFN-α in the animal.

For certain embodiments, the present invention provides a method of treating a neoplastic disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III to the animal.

For certain embodiments, the present invention provides a method of treating a neoplastic disease in an animal comprising administering a therapeutically effective amount of a compound or salt of any one of the above embodiments of Formulas I, II, and III, or a pharmaceutical composition comprising a therapeutically effective amount of a compound or salt of any one of the above embodiments of Formulas I, II, and III to the animal; and selectively inducing the biosynthesis of IFN-α in the animal.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene," and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula

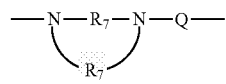

each $R_7$ group is independently selected. In another example, when more than one Y group is present, each Y group is independently selected. In a further example, when more than one —N($R_8$)-Q-$R_4$ group is present (e.g., more than one —Y—$R_4$ group is present, and both contain a —N($R_8$)-Q- group) each $R_8$ group is independently selected, each Q group is independently selected, and each $R_4$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Compounds (including intermediates) of the present invention may exist in different tautomeric forms, and all such forms are embraced within the scope of the invention. The term "tautomer" or "tautomeric form" refers to structural isomers of different energies, which are interconvertible via a low energy barrier. For example, proton tautomers (prototropic tautomers) include interconversions via migration of a proton, such as keto-enol and imine-enamine isomerizations. When compounds of the present invention have a hydrogen atom for the $R_2$ group, proton migration between the oxygen atom at the 2-position and the 3-position may occur. For example, the following Formulas $I_a$ and $I_b$ are tautomeric forms of each other, and Formulas $II_a$ and $II_b$ are tautomeric forms of each other:

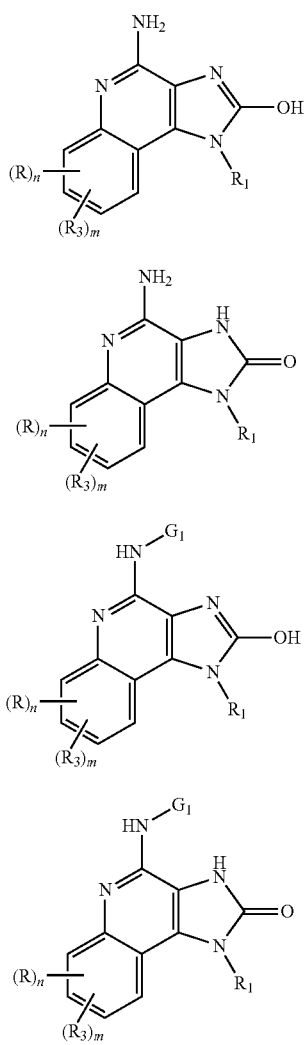

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R, $R_1$, $R_2$, and n are as defined above. In step (1) of Reaction Scheme I, a 2,4-dichloro-3-nitroquinoline of Formula V is reacted with an amine of Formula $R_1$—$NH_2$. The reaction can be conveniently carried out by adding the amine to a solution of a compound of Formula V in the presence of a base such as triethylamine. The reaction is carried out in a suitable solvent, such as dichloromethane, chloroform, or N,N-dimethylformamide (DMF) and may be carried out at room temperature, a subambient temperature such as 0° C., or an elevated temperature such as the reflux temperature of the solvent. Many 2,4-dichloro-3-nitropyridines of Formula V are known or can be prepared by known methods; see, for example, U.S. Pat. Nos. 4,988,815 (André et al) and 6,518,265 (Kato et al.). For example, they are readily prepared by chlorinating 3-nitroquinoline-2,4-diols with a chlorinating agent such as phosphorus(III) oxychloride; 3-nitroquinoline-2,4-diols are commercially available or can be prepared from substituted anilines according to the methods described in Kohler et al, *Chem. Ber.* 60, p. 1108 (1927); Buckle et al, *J. Med. Chem.*, 18, pp. 726-732 (1975), and Kappe et al, *J. Heterocyclic Chem.* 25, p. 857, (1988).

Numerous amines of Formula $R_1$—$NH_2$ are commercially available; others can be prepared by known methods. For example, a variety of substituted and unsubstituted arylalkylenyl amines and isomeric (aminomethyl)pyridines are commercially available. The synthesis of tetrahydro-2H-pyran-4-ylmethylamine hydrochloride, which can be used to prepare compounds of Formula VI wherein $R_1$ is a tetrahydro-2H- pyran-4-ylmethyl group, has been reported; see, U.S. Patent Application Publication No. 2004/0147543 (Hays et al.), Examples 477-480.

Other primary amines can be used in step (1) of Reaction Scheme I to provide, after subsequent synthetic transformations, compounds of Formula VI wherein $R_1$ is as defined above. For example, tert-butyl amine can be used in step (1) to provide a compound or salt of Formula VI with a tert-butyl group at the $R_1$ position, which can be converted to a compound of Formula VI wherein $R_1$ is hydrogen by heating the tert-butyl-substituted compound with hydrochloric acid in a suitable solvent such as methanol at an elevated temperature such as 75° C. In another example, an amino alcohol can be used in step (1) to provide a compound of Formula VI with a hydroxyalkyl group at the $R_1$ position. The hydroxy group can optionally be protected for subsequent steps in Reaction Scheme I and then deprotected and converted to a chloro group using conventional chlorination methods. A compound of Formula VI or IX with a chloroalkyl group at the $R_1$ position can be treated with a cyclic secondary amine to provide a compound in which $R_1$ is —$X_1$-Het. Many cyclic secondary amines are commercially available, such as unsubstituted or substituted pyrrolidines, piperidines, morpholines, and piperazines; others can be prepared using conventional methods. The reaction can be conveniently carried out by adding a cyclic secondary amine to a chloroalkyl substituted compound in a suitable solvent such as DMF. The reaction can be conveniently carried out in the presence of a base such as potassium carbonate at an elevated temperature such as 65° C. In another example, a compound of Formula VI wherein $R_1$ is —$X_1$—NH-Boc, in which Boc is tert-butoxycarbonyl, can be converted to a compound of Formula VI wherein $R_1$ is —$X_1$—N($R_8$)-Q-$R_4$ using one of the methods of Reaction Scheme IV below.

In step (2) of Reaction Scheme I, a compound of Formula VI is reduced to provide a 2-chloroquinoline-3,4-diamine of Formula VII. The reaction can be carried out by heterogeneous hydrogenation using platinum on carbon as the heterogeneous hydrogenation catalyst. The hydrogenation can be conveniently carried out in a Parr apparatus in a suitable solvent such as toluene, methanol, acetonitrile, or ethyl acetate. The reaction can be carried out at room temperature. The reduction can be carried out using alternative methods as described in U.S. Pat. No. 5,395,937 (Nikolaides et al). Several 2-chloroquinoline-3,4-diamines of Formula VII are known compounds. See, for example, U.S. Pat. Nos. 4,988,815 (André et al); 5,268,376 (Gerster); 5,756,747 (Gerster); 6,069,149 (Nanba et al); 6,518,265 (Kato et al.), 6,683,088 (Crooks et al); and 6,664,260 (Charles et al).

In step (3) of Reaction Scheme I, a 2-chloroquinoline-3,4-diamine of Formula VII is cyclized to provide a 4-chloro-1H-imidazo[4,5-c]quinolin-2-ol or 2-alkoxy-4-chloro-1H-imidazo[4,5-c]quinoline of Formula VIII. To prepare a compound of Formula VIII wherein $R_2$ is hydrogen, the cyclization can be conveniently carried out by combining a 2-chloroquinoline-3,4-diamine of Formula VII with 1,1'-carbonyldiimidazole in a suitable solvent such as tetrahydrofuran (THF), tert-butyl methyl ether, dichloromethane, or DMF. Optionally, the reaction can be carried out in the presence of a base such as pyridine. The reaction may be carried out at room temperature or, preferably, at an elevated temperature such as the reflux temperature of the solvent. Alternatively, to prepare a compound in which $R_2$ is $C_{1-4}$ alkyl or $C_{1-4}$ alkoxy$C_{2-4}$ alkylenyl, the cyclization can be conveniently carried out by combining a 2-chloroquinoline-3,4-diamine of Formula VII with an orthocarbonate, for example tetraethyl orthocarbonate, in a suitable solvent such as acetic acid. The reaction may be carried out at room temperature or at an elevated temperature such as 30° C. to 50° C.

In step (4) of Reaction Scheme I, a compound of Formula VIII is aminated to provide a 2-hydroxy- or 2-alkoxy-1H-imidazo[4,5-c]quinolin-4-amine of Formula IX, a subgenus of Formula I. The reaction is conveniently carried out by adding a solution of ammonia in a suitable solvent such as methanol to a compound of Formula VIII and heating the reaction at an elevated temperature such as 135° C. to 175° C., preferably 150° C. to 170° C.

Reaction Scheme I

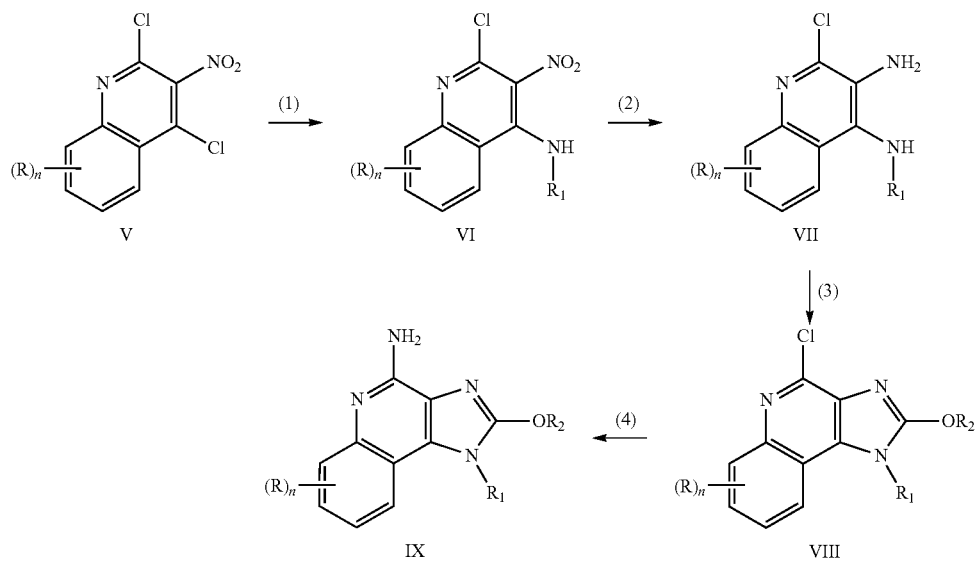

For some embodiments, compounds of the invention can be prepared according to Reaction Scheme II, wherein R, $R_1$, and n are as defined above, and $R_{2a}$ is selected from the group consisting of $C_{1-4}$ alkyl, hydroxy$C_{2-4}$ alkylenyl, and $C_{1-4}$ alkoxyC$_{2-4}$ alkylenyl. In step (1) of Reaction Scheme I, a quinoline-3,4-diamine of Formula X is cyclized to provide a 1,3-dihydro-1H-imidazo[4,5-c]quinoline-2-thione of Formula XI. The reaction can be carried out using 1,1'-thiocarbonyldiimidazole instead of 1,1'-carbonyldiimidazole under the conditions described in step (3) of Reaction Scheme I. Several quinoline-3,4-diamines of Formula X are known or can be prepared by known methods; see for example, U.S. Pat. Nos. 4,689,338 (Gerster), 5,268,376 (Gerster), 5,389,640 (Gerster et al.), 6,331,539 (Crooks et al.), 6,451,810 (Coleman et al.), 6,541,485 (Crooks et al.), 6,660,747 (Crooks et al.), 6,683,088 (Crooks et al.), 6,656,938 (Crooks et al.), and U.S. Patent Publication Application No. US 2004/0147543 (Hays et al.).

In step (2) of Reaction Scheme II, a 1,3-dihydro-1H-imidazo[4,5-c]quinoline-2-thione of Formula XI is methylated to provide a 2-(methylthio)-1H-imidazo[4,5-c]quinoline of Formula XII. The reaction can be conveniently carried out by combining a compound of Formula XI with iodomethane in a suitable solvent or solvent mixture, such as ethanol/water, in the presence of a base, such as ammonium hydroxide or sodium methoxide. The reaction can be carried out at room temperature.

In step (3) of Reaction Scheme II, a 2-(methylthio)-1H-imidazo[4,5-c]quinoline of Formula XII is oxidized to a 2-(methylsulfonyl)-1H-imidazo[4,5-c]quinoline-5N-oxide of Formula XIII using a conventional oxidizing agent capable of forming N-oxides and sulfones. The reaction is conveniently carried out at room temperature by combining at least three equivalents of 3-chloroperoxybenzoic acid with a solution of a compound of Formula XII in a solvent such as chloroform or dichloromethane.

In step (4) of Reaction Scheme II, a 2-(methylsulfonyl)-1H-imidazo[4,5-c]quinoline-5N-oxide of Formula XIII is aminated to provide a 2-(methylsulfonyl)-1H-imidazo[4,5-c]quinolin-4-amine of Formula XIV. Step (4) can be carried out by the activation of an N-oxide of Formula XIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XIII in a suitable solvent such as dichloromethane or chloroform and then adding p-toluenesulfonyl chloride. The reaction can be carried out at room temperature.

Steps (3) and (4) of Reaction Scheme II may be carried out as a one-pot procedure by adding 3-chloroperoxybenzoic acid to a solution of a compound of Formula XII in a solvent such as dichloromethane or chloroform and then adding ammonium hydroxide and p-toluenesulfonyl chloride without isolating the N-oxide compound of Formula XIII.

In step (5) of Reaction Scheme II, the methylsulfonyl group of a 2-(methylsulfonyl)-1H-imidazo[4,5-c]quinolin-4-amine of Formula XIV is displaced with an alkoxide of Formula —O—C$_{1-4}$ alkyl or —O—C$_{2-4}$ alkylene-O—C$_{1-4}$ alkyl. Some alkoxides of these formulas are commercially available, for example, as alkali metal salts. Other alkoxides of these formulas can be readily prepared by known methods. The reaction can be carried out by combining an alkoxide with a 2-(methylsulfonyl)-1H-imidazo[4,5-c]quinolin-4-amine of Formula XIV at room temperature in a suitable solvent such as methanol.

A compound of Formula IX or XV wherein R$_2$ or R$_{2a}$ is C$_{1-4}$ alkoxyC$_{2-4}$ alkylenyl, prepared by the methods described in Reaction Scheme I or II, can be converted to a compound wherein R$_2$ or R$_{2a}$ is hydroxyC$_{2-4}$ alkylenyl using conventional dealkylation methods. For example, demethylation can be carried out by treating a compound of Formula IX or XV wherein R$_2$ or R$_{2a}$ is C$_{1-4}$ alkoxyC$_{2-4}$ alkylenyl with boron tribromide in a suitable solvent such as dichloromethane at a sub-ambient temperature such as −78° C.

Reaction Scheme II

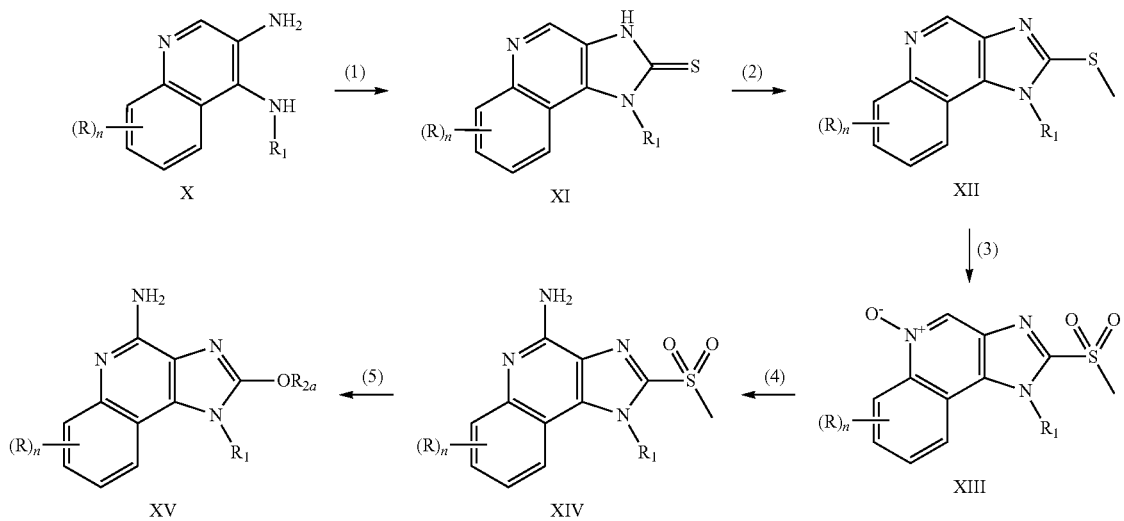

For some embodiments, compounds of the invention can be prepared according to Reaction Scheme III, wherein R, R$_1$, R$_2$, and R$_3$ are as defined above, n is 0 or 1, and D is —Br, —I, —OCH$_3$, or —OS(O)$_2$CF$_3$. Compounds of Formula XVI are available from the methods described in Reaction Scheme I or II starting with compounds of Formula V or X in which one of the R groups is —Br, —I, or —OCH$_3$. A compound of Formula XVI in which D is —OCH$_3$ can be converted in two steps to a compound of Formula XVI in which D is —OS(O)$_2$CF$_3$. In part (i), the methoxy group is demethylated to provide a hydroxy-substituted compound. The demethylation of a methoxy-substituted compound can be carried out with boron tribromide as described in of Reaction Scheme II. Alternatively, the demethylation can be carried out by heating the methoxy-substituted compound with anhydrous pyridinium chloride at an elevated temperature, such as 210° C. The resulting hydroxy group of is converted to a trifluoromethanesulfonate (triflate) group by reaction with trifluoromethanesulfonyl chloride, trifluoromethanesulfonic anhydride, or N-phenylbis(trifluoromethanesulfonimide), typically in the presence of a base, such as triethylamine. The reaction can be carried out in a suitable solvent such as dichloromethane, 1,2-dichloroethane, acetonitrile, THF, DMF, NMP, or pyridine. The reaction may be carried out at room temperature or an elevated temperature, such as the reflux temperature of the solvent.

When D is —Br, —I, or —OS(O)$_2$CF$_3$, a 2-hydroxy- or 2-alkoxy-1H-imidazo[4,5-c]quinolin-4-amine of Formula XVI can undergo known palladium-catalyzed coupling reactions such as the Suzuki coupling and the Heck reaction. For example, a compound of Formula XVI undergoes Suzuki coupling with a boronic acid of Formula R$_3$—B(OH)$_2$, an anhydride thereof, or a boronic acid ester of Formula R$_3$—B(O-alkyl)$_2$; wherein R$_3$ is —R$_{4b}$, —X$_a$—R$_4$, —X$_b$—Y—R$_4$, or —X$_b$—R$_5$; where X$_a$ is alkenylene; X$_b$ is arylene, heteroarylene, and alkenylene interrupted or terminated by arylene or heteroarylene; R$_{4b}$ is aryl or heteroaryl where the aryl or heteroaryl groups can be unsubstituted or substituted as defined in R$_4$ above; and R$_4$, R$_5$, and Y are as defined above; to provide a compound of Formula XVII, a subgenus of Formula I. Numerous boronic acids of Formula R$_3$—B(OH)$_2$, anhydrides thereof, and boronic acid esters of Formula R$_3$—B(O-alkyl)$_2$ are commercially available; others can be readily prepared using known synthetic methods.

The Heck reaction can also be used in Reaction Scheme III to provide compounds of Formula XVII, wherein R$_3$ is —X$_a$—R$_{4b}$ and —X$_a$—Y—R$_4$. The Heck reaction is carried out by coupling a compound of Formula XVI with a compound of the Formula H$_2$C=C(H)—R$_{4b}$ or H$_2$C=C(H)—Y—R$_4$. Several of these vinyl-substituted compounds are commercially available; others can be prepared by known methods. The Suzuki coupling and Heck reaction can be carried out according to any of the methods described in U.S. Patent Application Publication No. 2004/0147543 (Hays et al.).

Compounds of Formula XVII, wherein R$_3$ is —X$_c$—R$_4$, X$_c$ is alkynylene, and R$_4$ is as defined above, can also be prepared by palladium catalyzed coupling reactions such as the Stille coupling or Sonogashira coupling. These reactions are carried out by coupling a compound of Formula XVI with a compound of the Formula (alkyl)$_3$Sn—C≡C—R$_4$, (alkyl)$_3$Si—C≡C—R$_4$, or H—C≡C—R$_4$.

Compounds of Formula XVII prepared as described above by palladium-mediated coupling reactions, wherein R$_3$ is —X$_a$—R$_4$, —X$_a$—Y—R$_4$, —X$_{b2}$—Y—R$_4$, —X$_{b2}$—R$_5$, or —X$_c$—R$_4$, where X$_{b2}$ is alkenylene interrupted or terminated by arylene or heteroarylene, and X$_a$, X$_c$, Y, R$_4$, and R$_5$ are as defined above, can undergo reduction of the alkenylene or alkynylene group present to provide compounds of Formula XVII wherein R$_3$ is —X$_d$—R$_4$, —X$_d$—Y—R$_4$, —X$_e$—Y—R$_4$, or —X$_e$—R$_5$, where X$_d$ is alkylene; X$_e$ is alkylene interrupted or terminated by arylene or heteroarylene; and R$_4$, R$_5$, and Y are as defined above. The reduction can be carried out by hydrogenation according to the methods described in U.S. Patent Application Publication No. 2004/0147543 (Hays et al.).

Compounds of Formula XVI wherein D is —OCH$_3$ can be converted in Reaction Scheme III to compounds of Formula XVII wherein R$_3$ is —O—R$_{4b}$, —O—X—R$_4$, —O—X—Y—R$_4$, or —O—X—R$_5$; wherein R$_4$, R$_{4b}$, R$_5$, X, and Y are as defined above. When D is —OCH$_3$, the reaction shown in Reaction Scheme III is carried out in two parts. In part (i), the methoxy group is demethylated to provide a hydroxy-substituted compound. The demethylation can be carried out as described above. In part (ii), the hydroxy-substituted compound prepared in part (i) is converted to a compound of Formula XVII, wherein R$_3$ is —O—R$_{4b}$, —O—X—R$_4$, —O—X—Y—R$_4$, or —O—X—R$_5$, using a Williamson-type ether synthesis. The reaction is effected by treating a hydroxy-substituted 1H-imidazo[4,5-c]quinoline-2,4-diamine with an aryl, alkyl, or arylalkylenyl halide of Formula Halide-R$_{4b}$, Halide-alkylene-R$_4$, Halide-alkylene-Y—R$_4$, or Halide-alkylene-R$_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, and substituted fluorobenzenes. Other halides of these formulas can be prepared using conventional synthetic methods. The methods described in International Patent Application Publication Nos. WO2005/020999 (Lindstrom et al.) and WO2005/032484 (Lindstrom et al.) can be used.

Reaction Scheme III

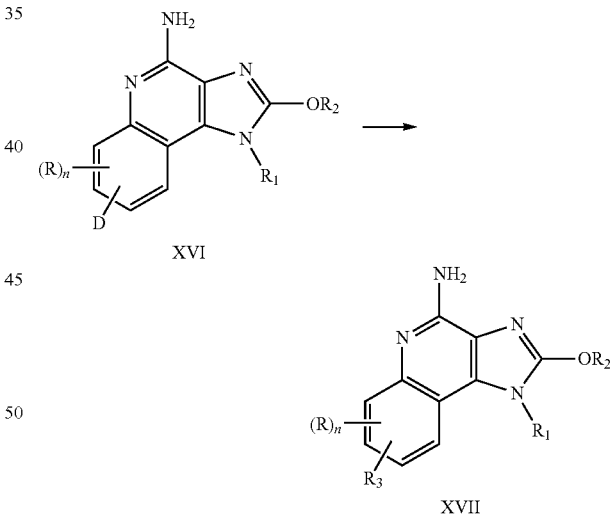

XVI

XVII

For some embodiments, compounds of the invention can be prepared according to Reaction Scheme IV, wherein R, R$_2$, and n are as defined above; Boc is tert-butoxycarbonyl; X$_3$ is X$_1$ or —CH(R$_{11}$)—Ar'—CH(R$_{11}$)—; and R$_{1b}$ is —X$_1$—N(R$_8$)-Q-R$_4$, —CH(R$_{11}$)—Ar'—CH(R$_{11}$)—N(R$_8$)-Q-R$_4$, or —CH(R$_{11}$)—Ar'—CH(R$_{11}$)—R$_5$, wherein R$_5$ is

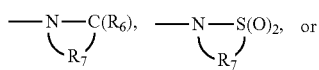

-continued

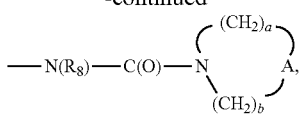

wherein $X_1$, $R_4$, $R_6$, $R_7$, $R_8$, $R_{11}$, Q, A, Ar', a, and b are as defined above. Compounds of Formula XVIII can be prepared according to the methods described in Reaction Scheme I, wherein an amine of Formula Boc-NH—$X_3$—$NH_2$ is employed in step (1) of Reaction Scheme I.

In step (1) of Reaction Scheme IV, the reaction conditions described in step (4) of Reaction Scheme I can be used to animate the 4-chloro group and simultaneously remove the Boc protecting group to provide a 1-amino-substituted 1H-imidazo[4,5-c]quinolin-4-amine of Formula XIX, a subgenus of Formula I.

In step (2) of Reaction Scheme IV, the 1-amino group in a compound of Formula XIX is treated with an acid chloride of Formula $R_4C(O)Cl$ or Cl—$R_7C(O)Cl$, a sulfonyl chloride of Formula $R_4S(O)_2Cl$ or Cl—$R_7S(O)_2Cl$, a sulfonic anhydride of Formula $(R_4S(O)_2)_{2-O}$, an isocyanate of Formula $R_4N=C=O$, $R_4(CO)N=C=O$, $R_4N=C=S$, or $R_4S(O)_2N=C=O$, a carbamoyl chloride of Formula $R_4N-(R_8)-C(O)Cl$ or

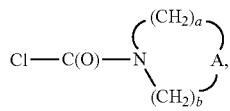

or a sulfamoyl chloride of Formula $R_4$—$N(R_8)$—$S(O)_2Cl$ to provide an amide, sulfonamide, urea, or sulfamide of Formula XX, a subgenus of Formula I. The reaction can be conveniently carried out by combining the acid chloride, sulfonyl chloride, sulfonic anhydride, or isocyanate and a solution of an amino-substituted compound, and a base such as triethylamine or N,N-diisopropylethylamine in a suitable solvent such as dichloromethane or N,N-dimethylacetamide (DMA). The reaction can be carried out at room temperature. When a chloroalkanesulfonyl chloride of Formula Cl—$R_7S(O)_2Cl$ or a chloroalkanoyl chloride of Formula Cl—$R_7C(O)Cl$ is used in this reaction, the isolable intermediate chloroalkanesulfonamide or chloroalkanamide can then be treated with a base such as 1,8-diazabicyclo[5.4.0]undec-7-ene (DBU) or sodium hydride at room temperature in a suitable solvent such as DMF to effect a cyclization and provide a compound of Formula XX in which $R_{1b}$ is —$CH(R_{11})$—Ar'—$CH(R_{11})$—$R_5$, wherein $R_5$ is

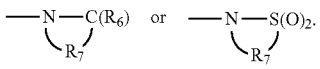

Reaction Scheme IV

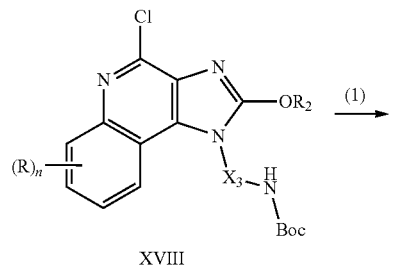

XVIII

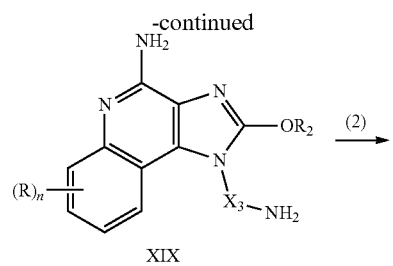

XIX

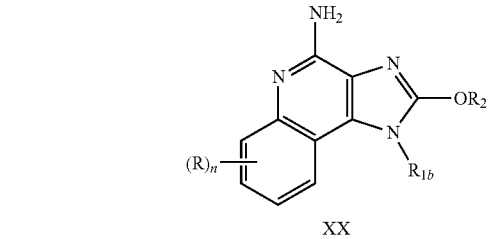

XX

For certain embodiments, compounds of the invention can be prepared according to Reaction Scheme V, wherein R, $R_1$, $R_2$, $R_3$, $G_1$, $G_2$, m, and n are as defined above. Compounds of Formula I can be prepared according to the methods of any of Reaction Schemes I through IV. Step (1) of Reaction Scheme V can be used to prepare a compound of Formula II. The amino group of a compound of Formula I can be converted by conventional methods to a functional group such as an amide, carbamate, urea, amidine, or another hydroylizable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")—R', —C(=NY')—R', —CH(OH)—C(O)—OY', —CH(OC$_{1-4}$ alkyl)Y$_0$, —CH$_2$Y$_1$, or —CH(CH$_3$)Y$_1$; wherein R' and R" are each independently $C_{1-10}$ alkyl, $C_{3-7}$ cycloalkyl, phenyl, or benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" may also be hydrogen; each α-aminoacyl group is independently selected from racemic, D, or L-amino acids; Y' is hydrogen, $C_{1-6}$ alkyl, or benzyl; Y$_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and Y$_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at room temperature.

Step (1a) of Reaction Scheme V can be used to prepare a compound of Formula III. The hydrogen atom of the alcohol group of a compound of Formula I can be replaced using conventional methods with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N-($C_{1-6}$ alkoxycarbonyl)aminomethyl, succinoyl, Cl_6 alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. Particularly useful compounds of Formula III are esters made from carboxylic acids containing one to six carbon atoms, unsubstituted or substituted benzoic acid esters, or esters made from naturally occurring amino acids. The reaction conditions described above in step (2) of Reaction Scheme IV can be used.

In some embodiments, compounds or salts of Formula I can be especially useful as immune response modifiers due to their ability to selectively induce IFN-α. As used herein, to "selectively induce IFN-α" means, that when tested according to the test methods described herein, the effective minimum concentration (of the compound or salt) for IFN-α induction is less than the effective minimum concentration for TNF-α induction. In some embodiments, the effective Reaction V

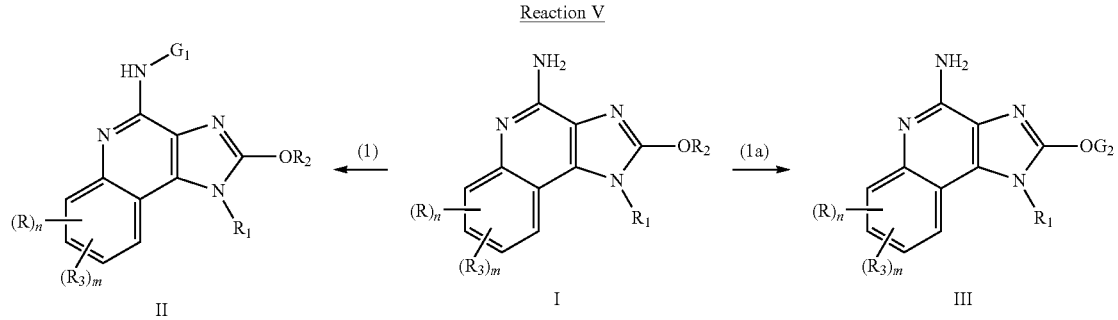

Compounds of the invention can also be prepared using variations of the synthetic routes shown in Reaction Schemes I through V that would be apparent to one of skill in the art. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, cytokine inhibition, immunomodulation, antitumor activity, and/or antiviral activity. Although the exact amount of compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful as immune response modifiers that can modulate the immune response in a number of different ways, rendering them useful in the treatment of a variety of disorders.

minimum concentration for IFN-α induction is at least 3-fold less than the effective minimum concentration for TNF-α induction. In some embodiments, the effective minimum concentration for IFN-α induction is at least 6-fold less than the effective minimum concentration for TNF-α induction. In other embodiments, the effective minimum concentration for IFN-α induction is at least 10-fold less than the effective minimum concentration for TNF-α induction. In other embodiments, the effective minimum concentration for IFN-α induction is at least 100-fold less than the effective minimum concentration for TNF-α induction. In some embodiments, when tested according to the test methods described herein, the amount TNF-α induced by compounds of the invention is at or below the background level of TNF-α in the test method. Compounds or salts of the invention may, therefore, provide a benefit, for example, a reduced inflammatory response, particularly when administered systemically, over compounds that also induce pro-inflammatory cytokines (e.g. TNF-α) or that induce pro-inflammatory cytokines at higher levels.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of Formula I, II, III, any of the embodiments described herein, or a combination thereof to the animal. An animal may also be vaccinated by administering an effective amount of a compound or salt of Formula I, II, III, any of the embodiments described herein, or a combination thereof to the animal as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography was carried out using a COMBIFLASH system (an automated high-performance flash purification product available from Teledyne Isco, Inc., Lincoln, Nebr., USA), a HORIZON HPFC system (an automated high-performance flash purification product available from Biotage, Inc, Charlottesville, Va., USA) or a combination thereof. For some of these purifications, either a FLASH 40+M silica cartridge or a FLASH 65i silica cartridge (both available from Biotage, Inc, Charlottesville, Va., USA) was used. The eluent used for each purification is given in the example.

Example 1

4-Amino-1-benzyl-1H-imidazo[4,5-c]quinolin-2-ol

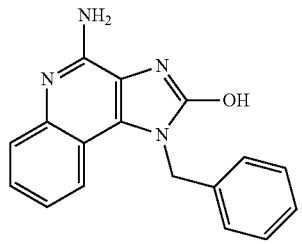 [SMILES: Nc1nc2ccccc2c2c1nc(O)n2Cc1ccccc1]

Part A

A solution of 2,4-dichloro-3-nitroquinoline (25 g, 0.10 mol) in N,N-dimethylformamide (DMF) (130 mL) was cooled to 0° C. Triethylamine (17.2 mL, 0.123 mol) and benzylamine (11.2 mL, 0.10 mol) were sequentially added, and the reaction was stirred at ambient temperature overnight. The reaction was poured into water (1 L), and the suspension was stirred for 30 minutes at room temperature. The resulting precipitate was isolated by filtration and washed with water to provide 31.92 g of N-benzyl-2-chloro-3-nitroquinolin-4-amine as a bright yellow powder.

Part B

N-Benzyl-2-chloro-3-nitroquinolin-4-amine (31.9 g, 0.102 mol), 5% platinum on carbon (3.2 g), and acetonitrile (325 mL) were added to a Parr vessel and shaken under hydrogen pressure (30 psi, $2.1 \times 10^5$ Pa) overnight. The mixture was filtered through a layer of CELITE filter agent, and the filtrate was concentrated under reduced pressure and further dried under high vacuum to provide 27.82 g of $N^4$-benzyl-2-chloroquinoline-3,4-diamine, which was used without purification.

Part C 1,1'-Carbonyldiimidazole (2.9 g, 18 mmol) was added to a solution of $N^4$-benzyl-2-chloroquinoline-3,4-diamine (5.0 g, 18 mmol) in tetrahydrofuran (THF) (50 mL), and the reaction was heated at 50° C. for three days. An analysis by liquid chromatography/mass spectrometry (LC/MS) indicated the presence of starting material, and additional 1,1'-carbonyldiimidazole (1.5 g, 9.2 mmol) was added. The reaction was stirred for several hours at 80° C., and additional 1,1'-carbonyldiimidazole (2.9 g, 18 mmol) was added. The reaction was stirred for one hour at 80° C. and overnight at 50° C. A solid was present and was isolated by filtration, washed with diethyl ether, and dried under vacuum to provide 3.48 g of 1-benzyl-1H-imidazo[4,5-c]quinolin-2-ol as a fluffy, white solid. Diethyl ether was added to the filtrate, and the resulting mixture was stirred for 20 minutes. A solid was present and was isolated by filtration and dried under vacuum to provide 0.95 g of 1-benzyl-4-chloro-1H-imidazo[4,5-c]quinolin-2-ol as a fluffy, beige solid.

Part D

1-Benzyl-4-chloro-1H-imidazo[4,5-c]quinolin-2-ol (approximately 1.1 g) and ammonia (approximately 100 mL of a 7 N solution in methanol) were added to a high-pressure vessel, which was sealed and heated in an oven at 170° C. for five days. The resulting solution was concentrated under reduced pressure, and the residue was purified by automated flash chromatography (silica cartridge, eluting with aqueous ammonium hydroxide:methanol:dichloromethane in a gradient from 0:0:100 to 0.2:4.8:95). A solid was present on top of the column; the solid was collected, washed with acetonitrile (6×100 mL), and purified again by automated flash chromatography (silica cartridge, eluting with aqueous ammonium hydroxide:methanol:dichloromethane in a gradient from 0.2:4.8:95 to 1:19:80) to provide 70 mg of 4-amino-1-benzyl-1H-imidazo[4,5-c]quinolin-2-ol as a white solid, mp greater than 250° C.

Anal. calcd. for $C_{17}H_{14}N_4O \cdot 0.3CH_4O$: C, 69.28; H, 5.11; N, 18.68. Found: C, 69.24; H, 5.15; N, 18.32.

Example 2

4-Amino-1-(pyridin-3-ylmethyl)-1H-imidazo[4,5-c]quinolin-2-ol

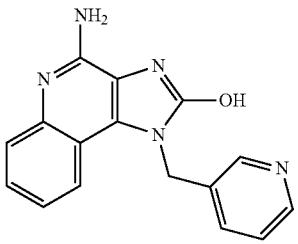 [SMILES: Nc1nc2ccccc2c2c1nc(O)n2Cc1cccnc1]

Part A

The method described in Part A of Example 1 was used to treat 2,4-dichloro-3-nitroquinoline (10.0 g, 40.8 mmol) in DMF (100 mL) with triethylamine (8.53 mL, 61.2 mmol) and 3-aminomethylpyridine (4.16 mL, 40.8 mmol). After the precipitate was isolated by filtration, it was dried for three hours in a vacuum oven at 60° C. to provide 13.0 g of 2-chloro-3-nitro-N-(pyridin-3-ylmethyl)quinolin-4-amine as a yellow solid.

Part B

2-Chloro-3-nitro-N-(pyridin-3-ylmethyl)quinolin-4-amine (13.0 g, 41.0 mmol), 5% platinum on carbon (1.3 g), and acetonitrile (60 mL) were added to a hydrogenation vessel and placed under hydrogen pressure (50 psi, $3.4 \times 10^5$ Pa) overnight. The mixture was filtered through a layer of CELITE filter agent, and the filter cake was washed with acetonitrile and methanol. The filtrate was concentrated under reduced pressure to provide 10.25 g of 2-chloro-$N^4$-(pyridin-3-ylmethyl)quinoline-3,4-diamine, which was used without purification.

Part C 1,1'-Carbonyldiimidazole (3.20 g, 19.7 mmol) was added to 2-chloro-$N^4$-(pyridin-3-ylmethyl)quinoline-3,4-diamine (5.09 g, 17.9 mmol) in THF (100 mL), and the resulting suspension was heated at 80° C. for three days. An analysis by LC/MS indicated the presence of starting material, and pyridine (100 mL) and additional 1,1'-carbonyldiimidazole (1 equivalent) were added. The reaction was stirred for two hours at 80° C., and additional 1,1'-carbonyldiimidazole (1 equivalent) was added. The reaction was stirred overnight at 80° C. and allowed to cool; a solid was present. Diethyl ether (50 mL) was added, and the solid was isolated by filtration and dried under vacuum to provide 4.2 g of 4-chloro-1-(pyridin-3-ylmethyl)-1H-imidazo[4,5-c]quinolin-2-ol as a gray solid.

Part D

4-Chloro-1-(pyridin-3-ylmethyl)-1H-imidazo[4,5-c]quinolin-2-ol (2.64 g, 8.52 mmol) and ammonia (40 mL of a 7 N solution in methanol) were added to a high-pressure vessel, which was sealed and heated in an oven at 165° C. for 42 hours and allowed to cool. A solid was present and was isolated by filtration washed with diethyl ether to provide 1.2 g of 4-amino-1-(pyridin-3-ylmethyl)-1H-imidazo[4,5-c]quinolin-2-ol. A second crop of solid (550 mg) was collected from the filtrate. A portion of the first crop was washed with dichloromethane, methanol, diethyl ether, and acetonitrile to provide a sample as tan needles, mp greater than 250° C.

Anal. calcd. for $C_{16}H_{13}N_5O$: C, 65.97; H, 4.50; N, 24.04. Found: C, 65.60; H, 4.20; N, 23.79.

Example 3

4-Amino-1-(4-methoxybenzyl)-1H-imidazo[4,5-c]quinolin-2-ol

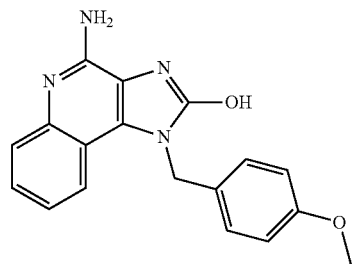 [SMILES: COc1ccc(Cn2c(O)nc3c(N)nc4ccccc4c32)cc1]

Part A

The method described in Part A of Example 1 was used to treat 2,4-dichloro-3-nitroquinoline (10.0 g, 40.8 mmol) in DMF (100 mL) with triethylamine (8.53 mL, 61.2 mmol) and 4-methoxybenzylamine (4.85 mL, 40.8 mmol). After the precipitate was isolated by filtration, it was dried for three hours in a vacuum oven at 60° C. to provide 13.1 g of 2-chloro-N-(4-methoxybenzyl)-3-nitroquinolin-4-amine as a brown solid.

Part B

The method of Part B of Example 2 was used to hydrogenate 2-chloro-N-(4-methoxybenzyl)-3-nitroquinolin-4-amine (13.0 g, 37.6 mmol) and provide 11.5 g of 2-chloro-$N^4$-(4-methoxybenzyl)quinoline-3,4-diamine as a dark oil.

Part C 1,1'-Carbonyldiimidazole (6.53 g, 40.3 mmol) was added to a solution of 2-chloro-$N^4$-(4-methoxybenzyl)quinoline-3,4-diamine (11.49 g, 36.62 mmol) and pyridine (75 mL) in THF (75 mL), and the reaction was heated at 80° C. overnight. An analysis by LC/MS indicated the presence of starting material, and additional 1,1'-carbonyldiimidazole (1 equivalent) was added. The reaction was stirred overnight at 80° C., and additional 1,1'-carbonyldiimidazole (1 equivalent) was added. The reaction was stirred overnight at 80° C. and allowed to cool, and the solvent was removed under reduced pressure. The residue was dissolved in dichloromethane (500 mL), and the resulting solution was washed sequentially with brine and water, dried over magnesium sulfate, filtered, and concentrated under reduced pressure to provide a solid. The solid was mixed with acetonitrile and isolated by filtration to provide 5.2 g of 4-chloro-1-(4-methoxybenzyl)-1H-imidazo[4,5-c]quinolin-2-ol.

Part D

4-Chloro-1-(4-methoxybenzyl)-1H-imidazo[4,5-c]quinolin-2-ol (2.0 g, 5.9 mmol) and ammonia (30 mL of a 7 N solution in methanol) were added to a high-pressure vessel, which was sealed and heated at 150° C. for two days. An analysis by LC/MS indicated the reaction was incomplete, and the vessel was sealed and heated at 165° C. for three days. The volatiles were removed under reduced pressure, and the residue was purified twice by automated flash chromatography (silica cartridge, eluting with aqueous ammonium hydroxide:methanol:dichloromethane in a gradient from 0:0:100 to 0.5:9.5:90). The resulting white solid was mixed with acetonitrile, isolated by filtration, and dried overnight under vacuum to provide 4-amino-1-(4-methoxybenzyl)-1H-imidazo[4,5-c]quinolin-2-ol as a white solid, mp greater than 260° C.

Anal. calcd. for $C_{18}H_{16}N_4O_2 \cdot 0.1H_2O$: C, 67.11; H, 5.07; N, 17.39. Found: C, 66.76; H, 4.90; N, 17.78.

Example 4

4-Amino-1-[(1R)-1-phenylethyl]-1H-imidazo[4,5-c]quinolin-2-ol

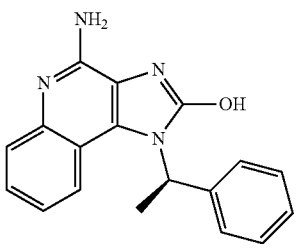 [SMILES: C[C@H](c1ccccc1)n1c(O)nc2c(N)nc3ccccc3c21]

Part A

The method described in Part A of Example 1 was used to treat 2,4-dichloro-3-nitroquinoline (20.6 g, 85.1 mmol) in DMF (100 mL) with triethylamine (35 mL, 0.225 mol) and (R)-(+)-α-methylbenzylamine (13.3 mL, 102 mmol). After the precipitate was isolated by filtration, it was washed with water and diethyl ether to provide 24.35 g of 2-chloro-3-nitro-N-[(1R)-1-phenylethyl]quinolin-4-amine as an orange solid.

Part B

The method of Part B of Example 1 was used to hydrogenate 2-chloro-3-nitro-N-[(1R)-1-phenylethyl]quinolin-4-amine (24.35 g, 73.3 mmol) with the modifications that the reaction was stopped after one hour, and magnesium sulfate was added to the mixture before filtration. 2-Chloro-$N^4$-[(1R)-1-phenylethyl]quinoline-3,4-diamine (21.0 g) was isolated as an amber oil.

Part C

THF (100 mL) and 1,1'-carbonyldiimidazole (8.1 g, 50.5 mmol) were sequentially added to a solution of 2-chloro-$N^4$-[(1R)-1-phenylethyl]quinoline-3,4-diamine (10.0 g, 33.6 mmol) in pyridine (100 mL), and the reaction was heated at 90° C. overnight. An analysis by LC/MS indicated the presence of starting material, and additional 1,1'-carbonyldiimidazole (6 equivalents) was added in portions as heating at 90° C. was continued for a second day. The reaction was cooled to approximately 0° C., and water (300 mL) was added. The mixture was stirred overnight. A precipitate was present and was isolated by filtration and washed with water and diethyl ether to provide 6.67 g of 4-chloro-1-[(1R)-1-phenylethyl]-1H-imidazo[4,5-c]quinolin-2-ol. A small portion of the product was triturated with hot acetonitrile, isolated by filtration, washed with cold acetonitrile and diethyl ether, and dried under vacuum to provide a white solid with the following analytical data, mp 227-229° C.

Anal. calcd. for $C_{18}H_{14}ClN_3O \cdot 0.5H_2O$: C, 64.97; H, 4.54; N, 12.63. Found: C, 65.15; H, 4.45; N, 12.68.

Part D

4-Chloro-1-[(1R)-1-phenylethyl]-1H-imidazo[4,5-c]quinolin-2-ol (3.87 g, 11.9 mmol) and ammonia (65 mL of a 7 N solution in methanol) were added to a high-pressure vessel, which was sealed and heated in an oven at 135° C. overnight. The reaction mixture was concentrated under reduced pressure, and the residue was purified by automated flash chromatography (silica cartridge, eluting with aqueous ammonium hydroxide:methanol:dichloromethane in a gradient from 0:0:100 to 0.2:4.8:95). The chromatographed product was triturated sequentially with hot acetonitrile, hot isopropanol, and hot ethanol and washed with diethyl ether after each trituration and filtration. The filtrates were combined, concentrated under reduced pressure, washed with diethyl ether, and dried in a vacuum oven overnight to provide 214 mg of 4-amino-1-[(1R)-1-phenylethyl]-1H-imidazo[4,5-c]quinolin-2-ol as tan needles, mp greater than 250° C.

Anal. calcd. for $C_{18}H_{16}N_4O \cdot 0.3H_2O$: C, 69.80; H, 5.40; N, 18.09. Found: C, 69.41; H, 5.63; N, 18.25.

Example 5

4-Amino-1-[(1S)-1-phenylethyl]-1H-imidazo[4,5-c]quinolin-2-ol

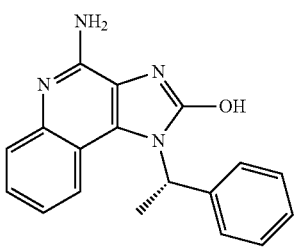 [SMILES: C[C@@H](c1ccccc1)n1c(O)nc2c(N)nc3ccccc3c21]

Part A

The method described in Part A of Example 1 was used to treat 2,4-dichloro-3-nitroquinoline (19.4 g, 78.5 mmol) in DMF (100 mL) with triethylamine (32 mL, 0.235 mol) and (S)-(−)-α-methylbenzylamine (11.5 g, 94.2 mmol) with the modification that the reaction was allowed to warm to room temperature and stirred for two hours. After the isolated precipitate was washed with water, it was dried under high vacuum overnight to provide 25.1 g of 2-chloro-3-nitro-N-[(1S)-1-phenylethyl]quinolin-4-amine as an orange solid.

Part B

The method of Part B of Example 4 was used to hydrogenate 2-chloro-3-nitro-N-[(1S)-1-phenylethyl]quinolin-4-amine (25 g, 76 mmol) to provide 2-chloro-$N^4$-[(1S)-1-phenylethyl]quinoline-3,4-diamine as an amber oil.

Part C

THF (100 mL) and 1,1'-carbonyldiimidazole (10.6 g, 65.6 mmol) were sequentially added to a solution of 2-chloro-$N^4$-[(1S)-1-phenylethyl]quinoline-3,4-diamine (13.0 g, 43.7 mmol) in pyridine (100 mL), and the reaction was heated at 90° C. for one hour. An analysis by LC/MS indicated the presence of starting material, and additional 1,1'-carbonyldiimidazole (3 equivalents) was added as heating at 90° C. was continued overnight. The reaction was still incomplete, and additional 1,1'-carbonyldiimidazole (3 equivalents) was added in portions as heating at 90° C. was continued for a second night. The reaction was cooled to approximately 0° C., and water (300 mL) was added. The mixture was stirred for two hours. A precipitate was present and was isolated by filtration, washed with water, and dried overnight in a vacuum oven to provide 9.98 g of 4-chloro-1-[(1S)-1-phenylethyl]-1H-imidazo[4,5-c]quinolin-2-ol.

Part D

4-Chloro-1-[(1S)-1-phenylethyl]-1H-imidazo[4,5-c]quinolin-2-ol (4.0 g, 12 mmol) and ammonia (65 mL of a 7 N solution in methanol) were added to a high-pressure vessel, which was sealed and heated in an oven at 135° C. over two nights. The volatiles were removed under reduced pressure. The crude product was purified twice by automated flash chromatography (silica cartridge, eluting with aqueous ammonium hydroxide:methanol:dichloromethane in a gradient from 0:0:100 to 0.2:3.8:96). The chromatographed product was washed with acetonitrile and diethyl ether several times and dried in a vacuum oven to provide 260 mg of 4-amino-1-[(1S)-1-phenylethyl]-1H-imidazo[4,5-c]quinolin-2-ol as an off-white solid, mp 292-295° C.

HRMS (EI) calcd for $C_{18}H_{16}N_4O$ (M+H): 305.1402. Found 305.1394.

Example 6

4-Amino-1-(tetrahydro-2H-pyran-4-ylmethyl)-1H-imidazo[4,5-c]quinolin-2-ol

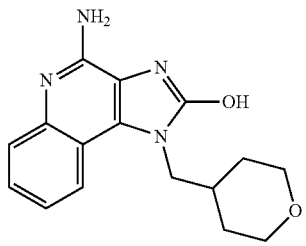 [SMILES: Nc1nc2ccccc2c2c1nc(O)n2CC1CCOCC1]

Part A

A solution of 2,4-dichloro-3-nitroquinoline (6 g, 25 mmol) in DMF (100 mL) was cooled to 0° C. Triethylamine (10.0 mL, 74.4 mmol) was added, and then tetrahydro-2H-pyran-4-ylmethylamine (see U.S. Patent Application Publication No. 2004/0147543 (Hays et al.) Examples 477-480) (3.4 g, 0.030 mol) was added slowly. Additional DMF was added, and the reaction was stirred at room temperature for one hour and cooled to 0° C. Water (300 mL) was added, and the mixture was maintained at 0° C. for 30 minutes. A precipitate was present and was isolated by filtration and washed sequentially with water and diethyl ether to provide 7 g of 2-chloro-3-nitro-N-(tetrahydro-2H-pyran-4-ylmethyl)quinolin-4-amine as a yellow solid.

Part B

The method of Part B of Example 1 was used to hydrogenate 2-chloro-3-nitro-N-(tetrahydro-2H-pyran-4-ylmethyl) quinolin-4-amine (7 g, 20 mmol) with the modifications that the reaction was stopped after four hours, and magnesium sulfate was added to the mixture before filtration. 2-Chloro-$N^4$-(tetrahydro-2H-pyran-4-ylmethyl)quinoline-3,4-diamine (5 g) was isolated as a sticky, amber solid.

Part C

THF (50 mL) and 1,1'-carbonyldiimidazole (4.2 g, 26 mmol) were sequentially added to a solution of 2-chloro-$N^4$-(tetrahydro-2H-pyran-4-ylmethyl)quinoline-3,4-diamine (5 g, 17 mmol) in pyridine (50 mL), and the reaction was heated at 90° C. overnight. The reaction was cooled to approximately 0° C., and water (400 mL) was added. The mixture was stirred for 30 minutes. A precipitate was present and was isolated by filtration and washed with water and diethyl ether to provide 4 g of 4-chloro-1-(tetrahydro-2H-pyran-4-ylmethyl)-1H-imidazo[4,5-c]quinolin-2-ol. A small portion of the product was triturated with hot acetonitrile, isolated by filtration, and washed with cold acetonitrile and diethyl ether to provide beige needles with the following analytical data, mp greater than 275° C.

Anal. calcd. for $C_{16}H_{16}ClN_3O_2$: C, 60.48; H, 5.08; N, 13.22. Found: C, 60.47; H, 5.09; N, 13.42.

Part D

4-Chloro-1-(tetrahydro-2H-pyran-4-ylmethyl)-1H-imidazo[4,5-c]quinolin-2-ol (3.9 g, 12 mmol) and ammonia (70 mL of a 7 N solution in methanol) were added to a high-pressure vessel, which was sealed and heated in an oven at 150° C. overnight. The volatiles were removed under reduced pressure. The crude product was purified by automated flash chromatography (silica cartridge, eluting with aqueous ammonium hydroxide:methanol:dichloromethane in a gradient from 0:0:100 to 0.4:7.6:92). The chromatographed product was triturated twice with hot acetonitrile, collected by filtration, and dried in a vacuum oven to provide 800 mg of 4-amino-1-(tetrahydro-2H-pyran-4-ylmethyl)-1H-imidazo[4,5-c]quinolin-2-ol as a white solid, mp greater than 250° C.

Anal. calcd. for $C_{16}H_{18}N_4O_2 \cdot 0.3H_2O$: C, 62.16; H, 6.62; N, 18.12. Found: C, 61.89; H, 6.29; N, 18.24.

Example 7

1-Benzyl-2-methoxy-1H-imidazo[4,5-c]quinolin-4-amine

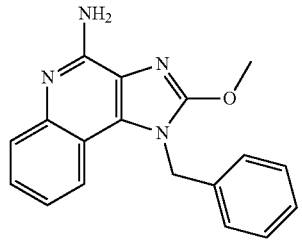 [SMILES: COc1nc2c(N)nc3ccccc3c2n1Cc1ccccc1]

Part A 1,1'-Thiocarbonyldiimidazole (5.74 g, 32.2 mmol) was added to a solution of $N^4$-benzylquinoline-3,4-diamine, see U.S. Pat. No. 4,689,338 (Gerster), Example 124, Parts A and B, (6.69 g, 26.8 mmol) in pyridine (50 mL) and THF (50 mL), and the reaction was heated at 80° C. for two hours and cooled to room temperature. A precipitate was present and was isolated by filtration and washed with diethyl ether to provide 4.17 g of 1-benzyl-1H-imidazo[4,5-c]quinoline-2-thiol as a white solid. The filtrate was treated with diethyl ether, and additional precipitate formed. The precipitate was isolated by filtration and washed with diethyl ether to provide an additional 1.90 g of product as a pale yellow solid.

Part B

1-Benzyl-1H-imidazo[4,5-c]quinoline-2-thiol (4.15 g, 14.2 mmol), deionized water (35 mL), ethanol (35 mL), and aqueous ammonium hydroxide (3.2 mL) were combined, and iodomethane (1.06 mL, 17.0 mmol) was added. The reaction was stirred at room temperature for one hour, and a precipitate formed. The precipitate was collected by filtration, washed with diethyl ether (5×100 mL), and dried under vacuum to provide 1-benzyl-2-(methylthio)-1H-imidazo[4,5-c]quinoline.

Part C

3-Chloroperoxybenzoic acid (5.0 g of 77% pure material) was added to a solution of the material from Part B in 1,2-dichloroethane (100 mL), and the reaction was stirred at room temperature overnight. Concentrated ammonium hydroxide (100 mL) and p-toluenesulfonyl chloride (2.78 g, 14.6 mmol) were sequentially added, and the reaction was stirred at room temperature for two hours. An analysis by LC/MS indicated the reaction was incomplete, and the aqueous layer was separated and extracted with ethyl acetate (100 mL) and chloroform (100 mL). The 1,2-dichloroethane and ethyl acetate fractions were combined and concentrated under reduced pressure. The residue was dissolved in 1,2-dichloroethane (100 mL), and 3-chloroperoxybenzoic acid (6.5 g of 77% pure material) was added. The reaction was stirred at room temperature overnight, and concentrated ammonium hydroxide (100 mL) and p-toluenesulfonyl chloride (2.78 g) were sequentially added. The reaction mixture was stirred for three hours at room temperature, and an analysis by LC/MS indicated the reaction was incomplete. Additional p-toluenesulfonyl chloride (2.7 g, 14.2 mmol) was added, and the reaction was stirred overnight at room temperature, diluted with deionized water (200 mL), and extracted with chloroform (2×200 mL) and ethyl acetate (2×200 mL). The combined extracts were concentrated under reduced pressure. The crude product (6.58 g) was purified twice by automated flash chromatography (silica cartridge, eluting with aqueous ammonium hydroxide:methanol:dichloromethane first in a gradient from 0:0:100 to 0.2:2.8:97 and second in a gradient from 0:0:100 to 0.2:3.8:96) to provide 890 mg of 1-benzyl-2-(methylsulfonyl)-1H-imidazo[4,5-c]quinolin-4-amine

Part D

A solution of 1-benzyl-2-(methylsulfonyl)-1H-imidazo[4,5-c]quinolin-4-amine (890 mg, 2.5 mmol) in methanol (10 mL) was stirred at room temperature for two minutes, and sodium methoxide (5 mL of a 25% w/w solution in methanol) was added. The resulting suspension was stirred at room temperature for one hour and then concentrated under reduced pressure. The residue was partitioned between ethyl acetate (200 mL) and water (150 mL). The organic layer was separated and dried over magnesium sulfate, filtered, and concentrated under reduced pressure. The crude product was purified by automated flash chromatography (silica cartridge, eluting with aqueous ammonium hydroxide:methanol:dichloromethane in a gradient from 0:0:100 to 0.3:4.7:95). The resulting off-white solid was triturated with hot acetonitrile, isolated by filtration, and dried under vacuum to provide 50 mg of 1-benzyl-2-methoxy-1H-imidazo[4,5-c]quinolin-4-amine as a white solid, mp 240-242° C.

Anal. calcd. for $C_{18}H_{16}N_4O \cdot 0.5H_2O$: C, 68.99; H, 5.47; N, 17.88. Found: C, 68.94; H, 5.33; N, 17.72.

Examples 8-55

Part A

Triethylamine (12.5 mL, 0.0889 mol) and 1-(N-Boc-aminomethyl)-3-(aminomethyl)benzene (17.71 g, 74.94 mmol) were sequentially added to a solution of 2,4-dichloro-3-nitroquinoline (18.2 g, 0.0750 mol) in DMF (90 mL), and the reaction was stirred at room temperature under nitrogen for 1.5 hours. The reaction was poured into water (2 L), and the suspension was stirred for 15 minutes. Most of the water was decanted away from the resulting precipitate, which was dissolved in ethyl acetate (600 mL). The ethyl acetate was separated from a small amount of remaining water and then removed under reduced pressure. The resulting solid was dried under vacuum to provide 38.24 g of tert-butyl 3-{[(2-chloro-3-nitroquinolin-4-yl)amino]methyl}benzylcarbamate as a sticky, amber solid.

Part B tert-Butyl 3-{[(2-chloro-3-nitroquinolin-4-yl)amino]methyl}benzylcarbamate (19.64 g, 44.34 mmol), 5% platinum on carbon (2.0 g), and acetonitrile (325 mL) were added to a Parr vessel and shaken under hydrogen pressure (30 psi, $2.1 \times 10^5$ Pa) overnight. The mixture was filtered, and the filtrate was concentrated under reduced pressure and further dried under high vacuum for 1.5 hours to provide 17.03 g of tert-butyl 3-{[(3-amino-2-chloroquinolin-4-yl)amino]methyl}benzylcarbamate as a thick, brown oil.

Part C

DMF (150 mL), pyridine (10 mL), and 1,1'-carbonyldiimidazole (16.7 g, 103 mmol) were added to tert-butyl 3-{[(3-amino-2-chloroquinolin-4-yl)amino]methyl}benzylcarbamate (17.03 g, 41.24 mmol), and the reaction was heated at 80° C. overnight and allowed to cool. The volatiles were removed under reduced pressure. The residue was mixed with ethyl acetate, collected by filtration, and dried under vacuum for two hours to provide 12.06 g of tert-butyl 3-[4-chloro-2-hydroxy-1H-imidazo[4,5-c]quinolin-1-yl)methyl]benzylcarbamate as a white solid.

Part D tert-Butyl 3-[(4-chloro-2-hydroxy-1H-imidazo[4,5-c]quinolin-1-yl)methyl]benzylcarbamate (8.04 g, 18.3 mmol) and ammonia (100 mL of a 7 N solution in methanol) were added to a high-pressure vessel, which was sealed and heated in an oven at 160° C. for five days and allowed to cool. The volatiles were removed under reduced pressure to provide 5.1 g of a mixture of tert-butyl 3-[(4-amino-2-hydroxy-1H-imidazo[4,5-c]quinolin-1-yl)methyl]benzylcarbamate and 4-amino-1-[(3-aminomethyl)benzyl]-1H-imidazo[4,5-c]quinolin-2-ol.

Part E

An acid chloride, sulfonyl chloride, isocyanate, or carbonyl chloride indicated in the table below (0.11 mmol, 1.1 equivalents) was added to a test tube containing a solution of N,N-diisopropylethylamine (53.2 µL, 0.305 mmol) and the material from Part E (53 mg, 0.099 mmol of 4-amino-1-[(3-aminomethyl)benzyl]-1H-imidazo[4,5-c]quinolin-2-ol) in N,N-dimethylacetamide (DMA) (1 mL). The tube was then capped and stirred overnight at room temperature. Two drops of water were added to the test tube, and the solvent was removed by vacuum centrifugation. For each of Examples 9-24, THF (1 mL) and a solution of lithium hydroxide monohydrate (12.5 mg) in water (1 mL) were added, and the reaction was stirred for four hours. The solvent was removed under reduced pressure. The compounds were purified by reversed phase preparative high-performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with nonlinear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

Examples 8-55

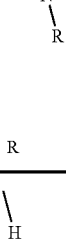

| Example | Reagent | R | Measured Mass (M + H) |
|---|---|---|---|
| 8 | None | 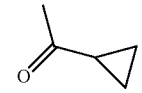 | 320.1523 |
| 9 | Cyclopropanecarbonyl chloride | 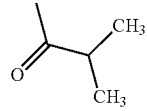 | 388.1776 |
| 10 | Isobutyryl chloride | 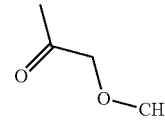 | 390.1935 |
| 11 | Methoxyacetyl chloride | 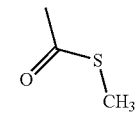 | 392.1736 |
| 12 | Methyl chlorothiolformate | 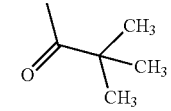 | 394.1336 |
| 13 | Pivaloyl chloride | 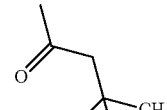 | 404.2069 |
| 14 | tert-Butylacetyl chloride | 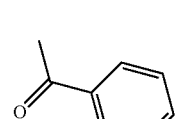 | 418.2271 |
| 15 | Benzoyl chloride |  | 424.1778 |

-continued
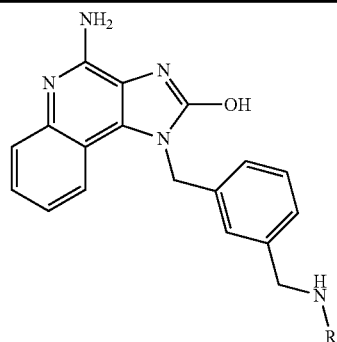
| Example | Reagent | R | Measured Mass (M + H) |
|---|---|---|---|
| 16 | m-Toluoyl chloride | 3-methylbenzoyl | 438.1951 |
| 17 | o-Toluoyl chloride | 2-methylbenzoyl | 438.1914 |
| 18 | p-Toluoyl chloride | 4-methylbenzoyl | 438.1934 |
| 19 | Phenylacetyl chloride | phenylacetyl | 438.1970 |
| 20 | Hydrocinnamoyl chloride | 3-phenylpropanoyl | 452.2054 |
| 21 | 2-Methoxybenzoyl chloride | 2-methoxybenzoyl | 454.1922 |
| 22 | 3-Methoxybenzoyl chloride | 3-methoxybenzoyl | 454.1878 |

-continued

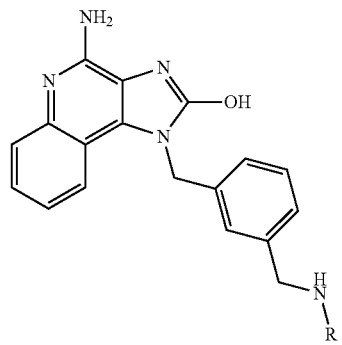

| Example | Reagent | R | Measured Mass (M + H) |
|---|---|---|---|
| 23 | Nicotinoyl chloride hydrochloride | 3-pyridyl C(=O)– | 425.1749 |
| 24 | Picolinoyl chloride hydrochloride | 2-pyridyl C(=O)– | 425.1733 |
| 25 | Ethanesulfonyl chloride | $CH_3CH_2SO_2$– | 412.1436 |
| 26 | 1-Propanesulfonyl chloride | $CH_3CH_2CH_2SO_2$– | 426.1606 |
| 27 | Isopropylsulfonyl chloride | $(CH_3)_2CHSO_2$– | 426.1619 |
| 28 | Dimethylsulfamoyl chloride | $(CH_3)_2NSO_2$– | 427.1544 |
| 29 | 1-Butanesulfonyl chloride | $CH_3(CH_2)_3SO_2$– | 440.1759 |
| 30 | Benzenesulfonyl chloride | $C_6H_5SO_2$– | 460.1444 |

-continued
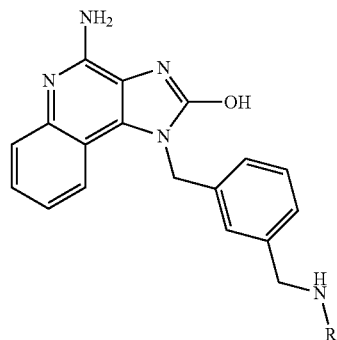
| Example | Reagent | R | Measured Mass (M + H) |
|---|---|---|---|
| 31 | 1-Methylimidazole-4-sulfonyl chloride | | 464.1525 |
| 32 | 3-Methylbenzenesulfonyl chloride | | 474.1624 |
| 33 | alpha-Toluenesulfonyl chloride | | 474.1591 |
| 34 | o-Toluenesulfonyl chloride | | 474.1638 |
| 35 | 2-Fluorobenzenesulfonyl chloride | | 478.1369 |
| 36 | 3-Fluorobenzenesulfonyl chloride | | 478.1348 |
| 37 | 4-Fluorobenzenesulfonyl chloride | | 478.1364 |
| 38 | 3-Methoxybenzenesulfonyl chloride | | 490.1538 |

-continued
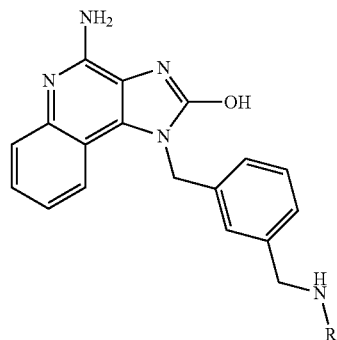
| Example | Reagent | R | Measured Mass (M + H) |
|---|---|---|---|
| 39 | 4-Methoxybenzenesulfonyl chloride | | 490.1590 |
| 40 | Isopropyl isocyanate | | 405.2065 |
| 41 | n-Propyl isocyanate | | 405.2060 |
| 42 | Isopropyl isothiocyanate | | 421.1824 |
| 43 | Cyclopentyl isocyanate | | 431.2187 |
| 44 | Cyclohexyl isocyanate | | 445.2370 |
| 45 | o-Tolyl isocyanate | | 453.2083 |

-continued
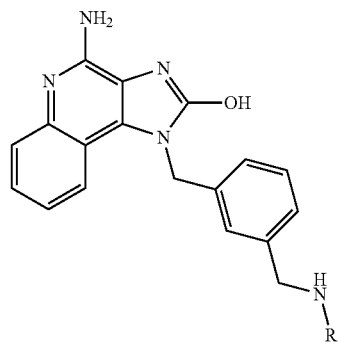
| Example | Reagent | R | Measured Mass (M + H) |
|---|---|---|---|
| 46 | 3-Pyridyl isothiocyanate | | 456.1620 |
| 47 | (R)-(+)-alpha-methylbenzyl isocyanate | | 467.2175 |
| 48 | (S)-(−)-alpha-methylbenzyl isocyanate | | 467.2210 |
| 49 | 2-Phenyl ethylisocyanate | | 467.2215 |
| 50 | N,N-Dimethylcarbamoyl chloride | | 391.1858 |
| 51 | 1-Pyrrolidinecarbonyl chloride | | 417.2053 |
| 52 | 1-Piperidinecarbonyl chloride | | 431.2189 |

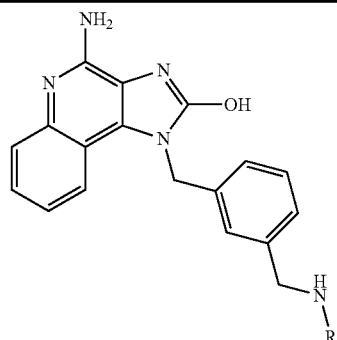

| Example | Reagent | R | Measured Mass (M + H) |
|---|---|---|---|
| 53 | 4-Morpholinylcarbonyl chloride | | 433.1979 |
| 54 | 4-Methyl-1-piperazinecarbonyl chloride | | 446.2298 |
| 55 | N-Methyl-N-phenylcarbamoyl chloride | | 453.2058 |

Examples 56-61

Part A

A solution of 2,4-dichloro-3-nitroquinoline (11.4 g, 47.1 mmol) in DMF (200 mL) was cooled to 0° C. Triethylamine (19.6 mL, 0.141 mol) and 1-(N-Boc-aminomethyl)-4-(aminomethyl)benzene (13.3 g, 56.5 mmol) were sequentially added, and the reaction was stirred for one hour and cooled again to 0° C. Water (300 mL) was added, and the mixture was stirred for 30 minutes at 0° C. and then extracted with dichloromethane. The dichloromethane fraction was concentrated under reduced pressure to provide 20 g of tert-butyl 4-{[(2-chloro-3-nitroquinolin-4-yl)amino]methyl}benzylcarbamate as a red oil.

Part B

The method of Part B of Example 1 was used to hydrogenate tert-butyl 4-{[(2-chloro-3-nitroquinolin-4-yl)amino]methyl}benzylcarbamate (20 g, 45 mmol) with the modification that magnesium sulfate was added to the mixture before filtration. tert-Butyl 4-{[(3-amino-2-chloroquinolin-4-yl)amino]methyl}benzylcarbamate (18 g) was isolated as a thick, orange-red oil.

Part C

The method of Part C of Example 6 was used to treat the material from Part B with 1,1'-carbonyldiimidazole (10.9 g, 67.7 mmol) in pyridine (100 mL) and THF (100 mL) with the modification that the isolated precipitate was purified by automated flash chromatography (silica cartridge, eluting with 3% methanol in dichloromethane) to provide tert-butyl 4-[(4-chloro-2-hydroxy-1H-imidazo[4,5-c]quinolin-1-yl)methyl]benzylcarbamate as a red oil.

Part D

The material from Part C and ammonia (70 mL of a 7 N solution in methanol) were added to a high-pressure vessel, which was sealed and heated in an oven at 150° C. overnight. The reaction mixture was filtered, and the collected solid was washed with acetonitrile. The filtrate was concentrated under reduced pressure, and the crude product (8 g) was purified by automated flash chromatography (silica cartridge, eluting with aqueous ammonium hydroxide:methanol:dichloromethane in a gradient from 0:0:100 to 1.5:28.5:70). The chromatographed product was triturated twice with hot acetonitrile, collected by filtration, and dried in a vacuum oven to provide 940 mg of 4-amino-1-[(4-aminomethyl)benzyl]-1H-imidazo[4,5-c]quinolin-2-ol.

Part E

An acid chloride, sulfonyl chloride, isocyanate, or carbonyl chloride indicated in the table below (0.11 mmol, 1.1 equivalents) was added to a test tube containing a solution of triethylamine (28.3 µL, 0.203 mmol) and 4-amino-1-[(4-aminomethyl)benzyl]-1H-imidazo[4,5-c]quinolin-2-ol (32.4 mg, 0.101 mmol) in DMA (1 mL). The tube was then capped and vortexed overnight at room temperature. Two drops of water were added to the test tube, and the solvent was removed by vacuum centrifugation. The compounds were purified by prep HPLC according to the method described in Examples 8-55. The table below shows the reagent used for each example, the structure of the resulting compound, and the observed accurate mass for the isolated trifluoroacetate salt.

Examples 56-61

| Example | Reagent | R | Measured Mass (M + H) |
|---|---|---|---|
| 56 | None | —H | 320.1508 |
| 57 | Methyl chloroformate | —C(=O)—O—CH$_3$ | 378.1559 |
| 58 | Cyclopropanecarbonyl chloride | —C(=O)-cyclopropyl | 388.1778 |
| 59 | Cyclopentanecarbonyl chloride | —C(=O)—NH-cyclopentyl | 431.2209 |
| 60 | N,N-Dimethylcarbamoyl chloride | —C(=O)—NH—CH$_3$ | 377.1730 |
| 61 | 4-Methyl-1-piperazinecarbonyl chloride | —C(=O)—N(piperazine)-CH$_3$ | 446.2274 |

Examples 62-88

Part A

A solution of 2,4-dichloro-3-nitroquinoline (32 g, 130 mmol) in DMF (100 mL) was cooled to 0° C. Triethylamine (27.5 mL, 198 mmol) was added, and 3-amino-1-propanol (11.9 g, 158 mmol) was slowly added. The reaction was stirred for two hours at room temperature and cooled again to 0° C. Water (300 mL) was added, and the mixture was stirred for 30 minutes at 0° C. A solid was present and was isolated by filtration, washed with water, and dried overnight in a vacuum oven to provide 34.5 g of 3-[(2-chloro-3-nitroquinolin-4-yl)amino]propan-1-ol as a yellow and orange solid.

Part B

The method of Part B of Example 1 was used to hydrogenate 3-[(2-chloro-3-nitroquinolin-4-yl)amino]propan-1-ol (10.0 g, 35.5 mmol) with the modifications that the reaction was stopped after one hour, and magnesium sulfate was added to the mixture before filtration. 3-[(3-Amino-2-chloroquinolin-4-yl)amino]propan-1-ol (10 g) was isolated as an amber oil and was combined with material made in separate experiments.

Part C 1,1'-Carbonyldiimidazole (25 g, 155 mmol) was added to a solution of 3-[(3-amino-2-chloroquinolin-4-yl)amino]propan-1-ol (26 g, 0.010 mol) in THF (140 mL), and the reaction was stirred for three hours at room temperature. Additional 1,1'-carbonyldiimidazole (25 g) and pyridine (50 mL) were added, and the reaction was heated at 90° C. for three hours and allowed to cool. The reaction was cooled to 0° C., and water (300 mL) was added. The resulting mixture was stirred for 30 minutes, and a precipitate formed. The precipitate was isolated by filtration and washed with water to provide 38 g of 3-(4-chloro-2-hydroxy-1H-imidazo[4,5-c]quinolin-1-yl)propyl 1H-imidazole-1-carboxylate as a white solid.

Part D

Aqueous sodium hydroxide (700 mL of 2 N) was added to a stirred suspension of 3-(4-chloro-2-hydroxy-1H-imidazo[4,5-c]quinolin-1-yl)propyl 1H-imidazole-1-carboxylate (38 g, 0.010 mol) in methanol (100 mL), and the resulting solution was stirred for two hours at room temperature and then adjusted to pH 7 with the addition of 10% w/w aqueous citric acid. A precipitate formed, and the mixture was stirred overnight. The precipitate was isolated by filtration and washed with acetonitrile to provide 24 g of 4-chloro-1-(3-hydroxypropyl)-1H-imidazo[4,5-c]quinolin-2-ol.

Part E

Phosphorus(III) oxychloride (7.9 g, 52 mmol) was added dropwise to a stirred solution of 4-chloro-1-(3-hydroxypropyl)-1H-imidazo[4,5-c]quinolin-2-ol (12 g, 43 mmol) in DMF (150 mL), and the reaction was stirred overnight at room temperature. An analysis by LC/MS indicated the presence of starting material, and additional phosphorus(III) oxychloride (7.9 g) was added. The reaction was stirred overnight at room temperature and then cooled to approximately 0° C. Water (300 mL) was slowly added, and a precipitate formed. The mixture was stirred for several minutes, and the precipitate was isolated by filtration, washed with water and diethyl ether, and dried in a vacuum oven to provide 8.2 g of 4-chloro-1-(3-chloropropyl)-1H-imidazo[4,5-c]quinolin-2-ol.

Part F

4-Chloro-1-(3-chloropropyl)-1H-imidazo[4,5-c]quinolin-2-ol (2.6 g, 8.8 mmol) and ammonia (65 mL of a 7 N solution in methanol) were added to a high-pressure vessel, which was sealed and heated in an oven at 150° C. for four days, allowed to cool, and concentrated under reduced pressure. The crude product was purified by column chromatography on silica gel (eluting with 20% methanol in dichloromethane). The resulting solid (2 g) was triturated with hot ethanol, collected by filtration, and washed with diethyl ether to provide 1.24 g of 4-amino-1-(3-aminopropyl)-1H-imidazo[4,5-c]quinolin-2-ol.

Part G

An acid chloride, sulfonyl chloride, isocyanate, or carbonyl chloride indicated in the table below (0.11 mmol, 1.1 equivalents) was added to a test tube containing a solution of N,N-diisopropylethylamine (42 μL, 0.24 mmol) and 4-amino-1-(3-aminopropyl)-1H-imidazo[4,5-c]quinolin-2-ol (25.8 mg, 0.100 mmol) in DMA (1 mL). The tube was then capped and vortexed overnight at room temperature. Two drops of water were added to the test tube, and the solvent was removed by vacuum centrifugation. The compounds were purified by prep HPLC according to the method described in Examples 8-55. The table below shows the reagent used for each example, the structure of the resulting compound, and the observed accurate mass for the isolated trifluoroacetate salt.

Examples 62-88

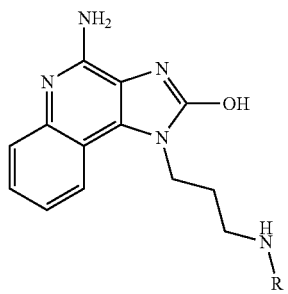

| Example | Reagent | R | Measured Mass (M + H) |
|---|---|---|---|
| 62 | None | H | 258.1354 |
| 63 | Benzoyl chloride | (benzoyl) | 362.1588 |
| 64 | 3-Methoxybenzoyl chloride | (3-methoxybenzoyl) | 392.1723 |
| 65 | 4-Methoxybenzoyl chloride | (4-methoxybenzoyl) | 392.1720 |
| 66 | 2-Chlorobenzoyl chloride | (2-chlorobenzoyl) | 396.1202 |
| 67 | Methanesulfonyl chloride | (methanesulfonyl) | 336.1131 |

-continued

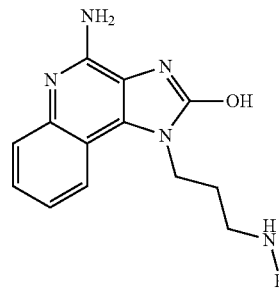

| Example | Reagent | R | Measured Mass (M + H) |
|---|---|---|---|
| 68 | Isopropylsulfonyl chloride | (isopropylsulfonyl) | 364.1430 |
| 69 | Dimethylsulfamoyl chloride | (dimethylsulfamoyl) | 365.1402 |
| 70 | Benzenesulfonyl chloride | (phenylsulfonyl) | 398.1273 |
| 71 | 1-Methylimidazole-4-sulfonyl chloride | (1-methylimidazol-4-ylsulfonyl) | 402.1340 |
| 72 | alpha-Toluenesulfonyl chloride | (benzylsulfonyl) | 412.1429 |
| 73 | 3-Cyanobenzenesulfonyl chloride | (3-cyanophenylsulfonyl) | 423.1237 |
| 74 | 4-Cyanobenzenesulfonyl chloride | (4-cyanophenylsulfonyl) | 423.1263 |
| 75 | 3-Methoxybenzenesulfonyl chloride | (3-methoxyphenylsulfonyl) | 428.1390 |
| 76 | 4-Methoxybenzenesulfonyl chloride | (4-methoxyphenylsulfonyl) | 428.1392 |

-continued

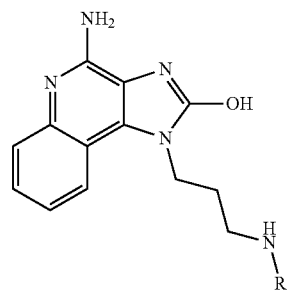

| Example | Reagent | R | Measured Mass (M + H) |
|---|---|---|---|
| 77 | 2-Chlorobenzenesulfonyl chloride | (2-chlorophenyl sulfonyl) | 432.0896 |
| 78 | 3-Pyridine sulfonyl chloride hydrochloride | (pyridin-3-yl sulfonyl) | 399.1214 |
| 79 | Isopropyl isocyanate | (isopropylcarbamoyl) | 343.1893 |
| 80 | Cyclopentyl isocyanate | (cyclopentylcarbamoyl) | 369.2038 |
| 81 | Phenyl isocyanate | (phenylcarbamoyl) | 377.1714 |
| 82 | 2-Methoxyphenyl isocyanate | (2-methoxyphenylcarbamoyl) | 407.1855 |
| 83 | 3-Methoxyphenyl isocyanate | (3-methoxyphenylcarbamoyl) | 407.1834 |

-continued

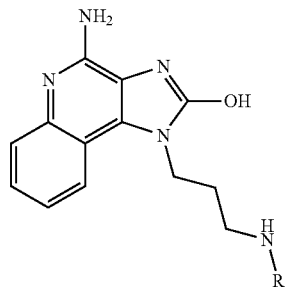

| Example | Reagent | R | Measured Mass (M + H) |
|---|---|---|---|
| 84 | 4-Methoxyphenyl isocyanate | acetamido-4-methoxyphenyl | 407.1842 |
| 85 | 2-Chlorophenyl isocyanate | acetamido-2-chlorophenyl | 411.1320 |
| 86 | 4-Chlorophenyl isocyanate | acetamido-4-chlorophenyl | 411.1330 |
| 87 | 1-Piperidinecarbonyl chloride | acetyl-piperidine | 369.2029 |
| 88 | 4-Morpholinylcarbonyl chloride | acetyl-morpholine | 371.1829 |

Examples 89-129

Part A

Triethylamine (31 g, 0.31 mol) was added to a solution of 2,4-dichloro-3-nitroquinoline (50 g of 90% pure material) in anhydrous DMF (400 mL). 4-Amino-1-butanol (21 mL, 0.23 mol) was added in portions over a period of ten minutes, and the reaction was stirred at room temperature overnight and then partitioned between deionized water (1.5 L) and ethyl acetate (800 mL). The organic layer was separated, and a precipitate formed. The precipitate was collected by filtration, and the filtrate was concentrated under reduced pressure to provide a solid. The two solids were dried under vacuum to provide 44.34 g of 4-(2-chloro-3-nitroquinolin-4-ylamino)butan-1-ol.

Part B

Triethylamine (83 mL, 0.60 mol) was added to a solution of 4-(2-chloro-3-nitroquinolin-4-ylamino)butan-1-ol (44.34 g, 149.9 mmol). A solution of tert-butyldimethylsilyl chloride (100 g of a 50% w/w solution in toluene, 0.33 mol) in DMF (60 mL) was slowly added, and the reaction was then stirred at room temperature of five hours. Additional tert-butyldimethylsilyl chloride (50 g of a 50% w/w solution in toluene) was added, and the reaction was stirred at room temperature for three days. Additional tert-butyldimethylsilyl chloride (100 g of a 50% w/w solution in toluene, 0.33 mol) was added, and the reaction was stirred at room temperature for three hours. Finally, additional triethylamine (83 mL, 0.60 mol) and tert-butyldimethylsilyl chloride (100 g of a 50% w/w solution in toluene, 0.33 mol) was added, and the reaction was stirred at room temperature for 1.5 hours. The reaction mixture was filtered to remove a solid, and the filtrate was concentrated under reduced pressure. The residue was dissolved in chloroform (250 mL), and the resulting solution was washed sequentially with 5% w/w aqueous ammonium chloride (3×150 mL), saturated aqueous sodium bicarbonate (2×150 mL), and brine (150 mL), dried over magnesium sulfate, filtered, and concentrated under reduced pressure. The resulting solid was further dried under vacuum and passed through a layer of silica gel (eluting with dichloromethane) to provide 56.04 g of N-[4-(tert-butyldimethylsilanyloxy)butyl]-2-chloro-3-nitroquinolin-4-amine as a yellow solid.

Part C

The method of Part B of Example 1 was used to hydrogenate N-[4-(tert-butyldimethylsilanyloxy)butyl]-2-chloro-3-nitroquinolin-4-amine (56.04 g, 136.7 mmol) with the modifications that the reaction was allowed to run for three days. $N^4$-[4-(tert-Butyldimethylsilanyloxy)butyl]-2-chloroquinoline-3,4-diamine (50.96 g) was isolated as a greenish-gray oil.

Part D 1,1'-Carbonyldiimidazole (32.6 g, 201 mmol) was added to a solution of $N^4$-[4-(tert-butyldimethylsilanyloxy)butyl]-2-chloroquinoline-3,4-diamine (50.96 g, 134.1 mmol), THF (250 mL), and pyridine (250 mL), and the reaction was heated at 80° C. overnight and allowed to cool. The volatiles were removed under reduced pressure. The residue was dissolved in ethyl acetate (600 mL), and the resulting solution was washed sequentially with brine (2×400 mL) and water (2×400 mL) and then concentrated under reduced pressure. The resulting solid was triturated with diethyl ether (1 L), collected by filtration, washed with diethyl ether (800 mL), and dried under vacuum for 30 minutes to provide 28.39 g of 1-[4-(tert-butyldimethylsilanyloxy)butyl]-4-chloro-1H-imidazo[4,5-c]quinolin-2-ol as a white solid.

Part E

1-[4-(tert-Butyldimethylsilanyloxy)butyl]-4-chloro-1H-imidazo[4,5-c]quinolin-2-ol (5.0 g, 12 mmol) and ammonia (200 mL of a 7 N solution in methanol) were added to a high-pressure vessel, which was sealed and heated in an oven at 150° C. for five days, allowed to cool, and concentrated under reduced pressure. The crude product was triturated with hexane for 15 minutes, and the resulting solid was isolated by filtration, washed with hexane (500 mL), and dried under vacuum to provide 3.53 g of 4-amino-1-(4-hydroxybutyl)-1H-imidazo[4,5-c]quinolin-2-ol as a light gray solid.

Part F

Thionyl chloride (1.1 mL, 15 mmol) was added to a solution of 4-amino-1-(4-hydroxybutyl)-1H-imidazo[4,5-c]quinolin-2-ol (3.5 g, 13 mmol) in 1,2-dichloroethane (60 mL), and the reaction was stirred at 50° C. overnight. A solid was present, which was collected by filtration and washed with diethyl ether (500 to 600 mL) to provide 3.24 g of 4-amino-1-(4-chlorobutyl)-1H-imidazo[4,5-c]quinolin-2-ol as a light gray solid.

Part G

An amine indicated in the table below (0.15 mmol, 1.5 equivalents) was added to a test tube containing a solution of N,N-diisopropylethylamine (50.4 μL, 0.29 mmol) and 4-amino-1-(4-chlorobutyl)-1H-imidazo[4,5-c]quinolin-2-ol (29.1 mg, 0.100 mmol) in DMA (1 mL). The tube was then capped and heated at 70° C. overnight. An analysis by LC/MS indicated the presence of starting material, and each tube was heated at 85° C. for 70 hours. The solvent was removed by vacuum centrifugation. The compounds were purified by prep HPLC according to the method described in Examples 8-55. The table below shows the reagent used for each example, the structure of the resulting compound, and the observed accurate mass for the isolated trifluoroacetate salt.

Examples 89-129

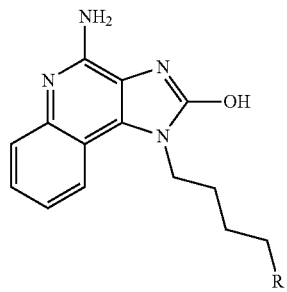

| Example | Reagent | R | Measured Mass (M + H) |
|---|---|---|---|
|  | None | \Cl | 291.1011 |

-continued
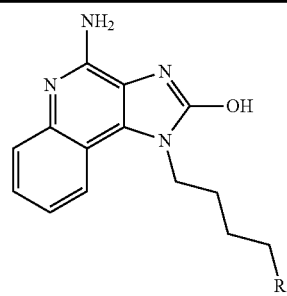
| Example | Reagent | R | Measured Mass (M + H) |
|---|---|---|---|
| 89 | 2-(Methylamino)ethanol | $H_3C-N(CH_3)-CH_2CH_2-OH$ | 330.1917 |
| 90 | Piperidine | piperidin-1-yl | 340.2159 |
| 91 | Morpholine | morpholin-4-yl | 342.1935 |
| 92 | 2-Ethylaminoethanol | $H_3C-CH_2-N(-)-CH_2CH_2-OH$ | 344.2098 |
| 93 | Hexamethyleneimine | azepan-1-yl | 354.2290 |
| 94 | 1-Methylpiperazine | 4-methylpiperazin-1-yl | 355.2263 |
| 95 | 3-Hydroxypiperidine | 3-hydroxypiperidin-1-yl | 356.2075 |
| 96 | 4-Hydroxypiperidine | 4-hydroxypiperidin-1-yl | 356.2084 |

-continued

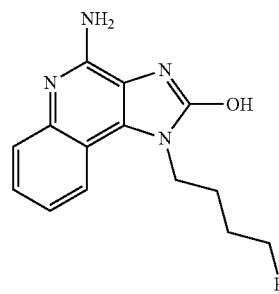

| Example | Reagent | R | Measured Mass (M + H) |
|---|---|---|---|
| 97 | 2-(Propylamino)ethanol | —N(CH₂CH₂CH₃)CH₂CH₂OH | 358.2240 |
| 98 | Thiomorpholine | thiomorpholin-4-yl | 358.1685 |
| 99 | Diethanolamine | —N(CH₂CH₂OH)₂ | 360.2058 |
| 100 | N-Methylfurfurylamine | —N(CH₃)CH₂-(2-furyl) | 366.1954 |
| 101 | N-Propylcyclopropanemethylamine | —N(CH₂CH₂CH₃)CH₂-cyclopropyl | 368.2451 |
| 102 | 3-(Dimethylamino)pyrrolidine | 1-methylpyrrolidin-3-yl (3-N(CH₃)₂) | 369.2390 |
| 103 | N,N'-Dimethyl-3-aminopyrrolidine | —N(CH₃)-(1-methylpyrrolidin-3-yl) | 369.2429 |

-continued

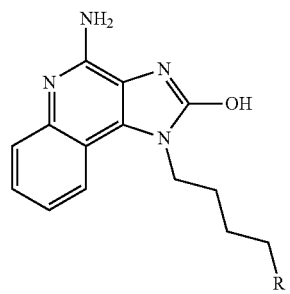

| Example | Reagent | R | Measured Mass (M + H) |
|---|---|---|---|
| 104 | N-Ethylpiperazine | *piperazine with N-ethyl* | 369.2435 |
| 105 | N-Methylhomopiperazine | *homopiperazine with N-methyl* | 369.2408 |
| 106 | 2-Piperidinemethanol | *2-(hydroxymethyl)piperidine* | 370.2253 |
| 107 | 3-(Hydroxymethyl)piperidine | *3-(hydroxymethyl)piperidine* | 370.2218 |
| 108 | 4-(Hydroxymethyl)piperidine | *4-(hydroxymethyl)piperidine* | 370.2214 |
| 109 | N-(2-Methoxyethyl)-N-propylamine | *N-propyl-N-(2-methoxyethyl)amine* | 372.2387 |

-continued
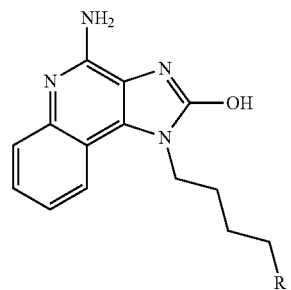
| Example | Reagent | R | Measured Mass (M + H) |
|---|---|---|---|
| 110 | N-N-Butylethanolamine | | 372.2402 |
| 111 | 3-Azabicyclo[3.2.2]nonane | | 380.2464 |
| 112 | 1-Methyl-4-(methylamino)piperidine | | 383.2569 |
| 113 | 2-Piperidineethanol | | 384.2388 |
| 114 | 4-Piperidineethanol | | 384.2377 |
| 115 | N-(2-Hydroxyethyl)piperazine | | 385.2347 |

-continued
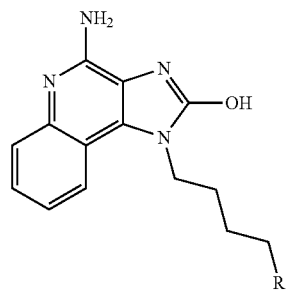
| Example | Reagent | R | Measured Mass (M + H) |
|---|---|---|---|
| 116 | 2-(N-Amylamino)ethanol | | 386.2575 |
| 117 | 1,2,3,4-Tetrahydroisoquinoline | | 388.2156 |
| 118 | (R)-(+)-N-Methyl-1-Phenylethylamine | | 390.2317 |
| 119 | (S)-(−)-N-Methyls-1-phenylethylamine | | 390.2321 |
| 120 | N-Methylphenethylamine | | 390.2254 |
| 121 | 2-(2-Methylaminoethyl)pyridine | | 391.2275 |

-continued

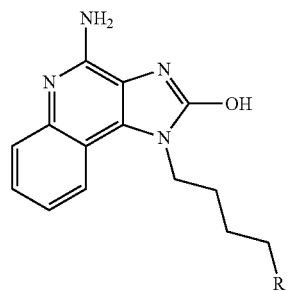

| Example | Reagent | R | Measured Mass (M + H) |
|---|---|---|---|
| 122 | 4-(EthylaminoMethyl)pyridine | [N-ethyl-N-(pyridin-4-ylmethyl)amino]methyl group | 391.2264 |
| 123 | N-Phenylethanolamine | N-(2-hydroxyethyl)-N-phenylamino group | 392.2104 |
| 124 | Decahydroisoquinoline | decahydroisoquinolin-2-yl | 394.2645 |
| 125 | N-Cyclohexylethanolamine | N-cyclohexyl-N-(2-hydroxyethyl)amino | 398.2541 |
| 126 | DL-alpha-(Methylaminomethyl)benzyl alcohol | N-methyl-N-(2-hydroxy-2-phenylethyl)amino | 406.2273 |
| 127 | N-Benzylethanolamine | N-benzyl-N-(2-hydroxyethyl)amino | 406.2227 |
| 128 | 1,3,3-Trimethyl-6-azabicyclo[3.2.1]octane | 1,3,3-trimethyl-6-azabicyclo[3.2.1]oct-6-yl | 408.2798 |

-continued

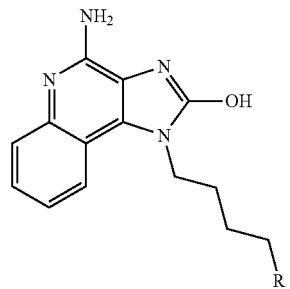

| Example | Reagent | R | Measured Mass (M + H) |
|---------|---------|---|------------------------|
| 129 | 1-Cyclohexylpiperazine | 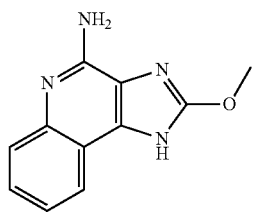 | 423.2834 |

Example 130

2-Methoxy-1H-imidazo[4,5-c]quinolin-4-amine

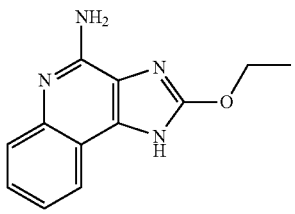 [SMILES: CCOc1nc2c(N)nc3ccccc3c2[nH]1]

Part A

Tetramethyl orthocarbonate (1.24 mL, 9.3 mmol) was added to a suspension of 2-chloroquinoline-3,4-diamine, see U.S. Pat. No. 5,756,747 (Gerster) Example 30, (1.5 g, 7.75 mmol) in acetic acid (8 mL), and the reaction was stirred overnight at room temperature. An analysis by LC/MS indicated the reaction was incomplete, and additional tetramethyl orthocarbonate (0.5 equivalent) was added. The reaction was stirred overnight at room temperature and diluted with water (100 mL). The mixture was adjusted to pH 7 with the addition of 2 N aqueous sodium hydroxide. Dichloromethane (100 mL) was added to the mixture, and a precipitate formed. The precipitate was isolated by filtration to provide 1.13 g of 4-chloro-2-methoxy-1H-imidazo[4,5-c]quinoline as a gray solid.

Part B

4-Chloro-2-methoxy-1H-imidazo[4,5-c]quinoline (700 mg) was added to a high-pressure vessel with ammonia (40 mL of a 7 N solution in methanol), and the vessel was sealed and heated at 150° C. for 24 hours, allowed to cool, and concentrated under reduced pressure. The crude product was purified twice by automated flash chromatography (silica cartridge, eluting with aqueous ammonium hydroxide: methanol:dichloromethane first in a gradient from 0:0:100 to 0.3:4.7:95 and secondly in a gradient from 0:0:100 to 0.2:3.8: 96) to provide 20 mg of 2-methoxy-1H-imidazo[4,5-c]quino-lin-4-amine as a white solid. The compound was further purified by prep HPLC according to the method described in Examples 8-55. The observed accurate mass (M+H) for the isolated trifluoroacetate salt was 215.0931.

Example 131

2-Ethoxy-1H-imidazo[4,5-c]quinolin-4-amine

Part A

The method described in Part A of Example 132 was used with the following modifications. Tetraethyl orthocarbonate (1.95 mL, 9.3 mmol) was used instead of tetramethyl orthocarbonate. When the reaction was incomplete after stirring overnight, no additional tetraethyl orthocarbonate was added, but the reaction was instead heated overnight at 40° C. The product did not precipitate when dichloromethane was added, and the dichloromethane layer was separated, dried over magnesium sulfate, filtered, and concentrated under reduced pressure to provide 720 mg of 4-chloro-2-ethoxy-1H-imidazo[4,5-c]quinoline as a white powder.

Part B

4-Chloro-2-ethoxy-1H-imidazo[4,5-c]quinoline (500 mg) was added to a high-pressure vessel with ammonia (40 mL of a 7 N solution in methanol), and the vessel was sealed and heated at 150° C. overnight. An analysis by LC/MS indicated the presence of starting material, and the reaction was heated at 150° C. for an additional four hours, allowed to cool, and concentrated under reduced pressure. The crude product was purified twice by automated flash chromatography (silica cartridge, eluting with aqueous ammonium hydroxide: methanol:dichloromethane in a gradient from 0:0:100 to 0.4: 7.6:92) to provide 52 mg of 2-ethoxy-1H-imidazo[4,5-c] quinolin-4-amine as a white solid.

MS m/z 229.17 (M+H)$^+$.

Exemplary Compounds

Certain exemplary compounds, including some of those described above in the Examples, have the following Formula ($I_c$) and an $R_{1a}$ and an $R_{1a}$ substituent shown in the following table, wherein each line of the table is matched with the Formula ($I_c$) to represent a specific embodiment of the invention.

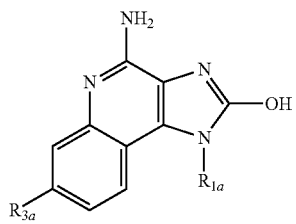

$I_c$

| $R_{1a}$ | $R_{3a}$ |
|---|---|
| benzyl | hydrogen |
| 4-methoxybenzyl | hydrogen |
| 1-phenylethyl | hydrogen |
| pyridin-3-ylmethyl | hydrogen |
| tetrahydro-2H-pyran-4-ylmethyl | hydrogen |
| benzyl | pyridin-3-yl |
| 4-methoxybenzyl | pyridin-3-yl |
| 1-phenylethyl | pyridin-3-yl |
| pyridin-3-ylmethyl | pyridin-3-yl |
| tetrahydro-2H-pyran-4-ylmethyl | pyridin-3-yl |
| benzyl | 3-hydroxyphenyl |
| 4-methoxybenzyl | 3-hydroxyphenyl |
| 1-phenylethyl | 3-hydroxyphenyl |
| pyridin-3-ylmethyl | 3-hydroxyphenyl |
| tetrahydro-2H-pyran-4-ylmethyl | 3-hydroxyphenyl |
| benzyl | 4-hydroxymethylphenyl |
| 4-methoxybenzyl | 4-hydroxymethylphenyl |
| 1-phenylethyl | 4-hydroxymethylphenyl |
| pyridin-3-ylmethyl | 4-hydroxymethylphenyl |
| tetrahydro-2H-pyran-4-ylmethyl | 4-hydroxymethylphenyl |
| benzyl | benzyloxy |
| 4-methoxybenzyl | benzyloxy |
| 1-phenylethyl | benzyloxy |
| pyridin-3-ylmethyl | benzyloxy |
| tetrahydro-2H-pyran-4-ylmethyl | benzyloxy |

Compounds of the invention have been found to modulate cytokine biosynthesis by inducing the production of interferon α, or interferon α and tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10$^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells (High Throughput Screen)

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemiluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of the Formula I:

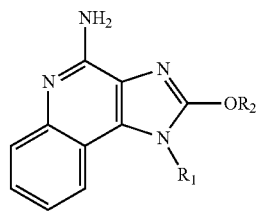

I wherein:
$R_2$ is selected from the group consisting of hydrogen, $C_{1-4}$ alkyl, hydroxy$C_{2-4}$ alkylenyl, and $C_{1-4}$ alkoxy$C_{2-4}$ alkylenyl;
$R_1$ is selected from the group consisting of:
  hydrogen,
  —CH($R_{11}$)—Ar,
  —CH($R_{11}$)—Ar'—$R_4$,
  —CH($R_{11}$)—Ar'—Y—$R_4$,
  —CH($R_{11}$)—Ar'—CH($R_{11}$)—Y—$R_4$,
  —CH($R_{11}$)—Ar'—$R_5$,
  —CH($R_{11}$)—Ar'—CH($R_{11}$)—$R_5$,
  —$X_1$-Het, and
  —$X_1$—N($R_8$)-Q-$R_4$;

Ar is selected from the group consisting of aryl and heteroaryl each of which is unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, cyano, amino, alkylamino, and dialkylamino;

Ar' is selected from the group consisting of arylene and heteroarylene each of which is unsubstituted or substituted by one or more substituents independently selected from the group consisting of alkyl, alkenyl, alkoxy, haloalkyl, haloalkoxy, halogen, nitro, hydroxy, hydroxyalkyl, cyano, amino, alkylamino, and dialkylamino;

Het is heterocyclyl which is unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

$X_1$ is $C_{1-6}$ alkylene that is optionally interrupted by one or more —O— groups;

$R_{11}$ is selected from the group consisting of hydrogen and $C_{1-3}$ alkylene;

Y is selected from the group consisting of:
  —O—,
  —S(O)$_{0-2}$—,
  —S(O)$_2$—N($R_8$)—,
  —C($R_6$)—,
  —C($R_6$)—O—,
  —O—C($R_6$)—,
  —O—C(O)—O—,
  —N($R_8$)-Q-,
  —C($R_6$)—N($R_8$)—,
  —O—C($R_6$)—N($R_8$)—,
  —C($R_6$)—N(O$R_9$)—,
  —O—N($R_8$)-Q-,
  —O—N=C($R_4$)—,
  —C(=N—O—$R_8$)—,
  —CH(—N(—O—$R_8$)-Q-$R_4$)—,

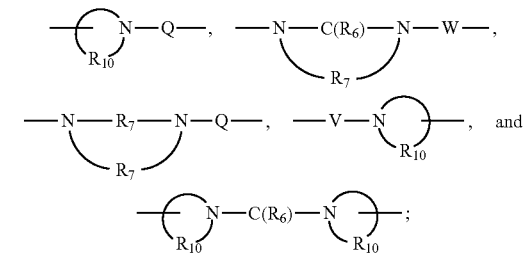

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen;

nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

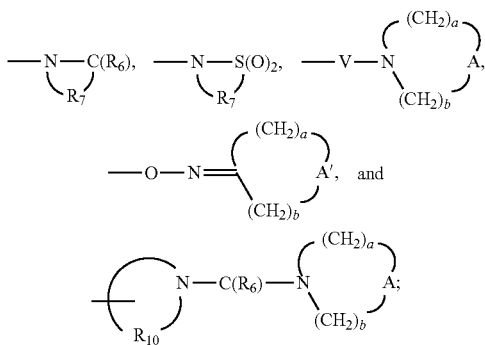

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
or a pharmaceutically acceptable salt thereof.

2. The compound or salt of claim 1 wherein $R_2$ is hydrogen.
3. The compound or salt of claim 1 wherein $R_2$ is $C_{1-4}$ alkyl.
4. The compound or salt of claim 1 wherein $R_2$ is ethyl or propyl, and $R_1$ is hydrogen.
5. The compound or salt of claim 1 wherein $R_1$ is —CH(R$_{11}$)—Ar.
6. The compound or salt of claim 5 wherein $R_{11}$ is hydrogen and Ar is phenyl.
7. The compound or salt of claim 5 wherein $R_{11}$ is hydrogen and Ar is pyridinyl.
8. The compound or salt of claim 5 wherein $R_1$ is selected from the group consisting of benzyl, 1-phenylethyl, and pyridinylmethyl, each of which is unsubstituted or substituted by one or more substituents independently selected from the group consisting of alkyl, alkoxy, haloalkyl, haloalkoxy, and halogen.
9. The compound or salt of claim 8 wherein $R_1$ is selected from the group consisting of benzyl, 4-methoxybenzyl, 1-phenylethyl, and pyridin-3-ylmethyl.
10. The compound or salt of claim 1 wherein $R_1$ is —CH(R$_{11}$)—Ar'—R$_4$.
11. The compound or salt of claim 10 wherein:
$R_{11}$ is hydrogen;
Ar' is phenylene; and
$R_4$ is selected from the group consisting of alkyl, aryl, heteroaryl, and arylalkylenyl
wherein alkyl, aryl, and heteroaryl are each unsubstituted or substituted by one or more substituents independently selected from the group consisting of alkyl, alkoxy, and halogen.
12. The compound or salt of claim 1 wherein $R_1$ is —CH(R$_{11}$)—Ar'—Y—R$_4$.
13. The compound or salt of claim 12 wherein:
$R_{11}$ is hydrogen;
Ar' is phenylene;
Y is —O—; and
$R_4$ is selected from the group consisting of alkyl, aryl, heteroaryl, and arylalkylenyl
wherein alkyl, aryl, and heteroaryl are each unsubstituted or substituted by one or more substituents independently selected from the group consisting of alkyl, alkoxy, and halogen.
14. The compound or salt of claim 1 wherein $R_1$ is tetrahydro-2H-pyran-4-ylmethyl.
15. The compound or salt of claim 1 wherein the compound is 4-amino-1-benzyl-1H-imidazo[4,5-c]quinolin-2-ol, or a pharmaceutically acceptable salt thereof.
16. The compound or salt of claim 1 wherein the compound is 4-amino-1-(pyridine-3-ylmethyl)-1H-imidazo[4,5-c]quinolin-2-ol, or a pharmaceutically acceptable salt thereof.
17. The compound or salt of claim 1 wherein the compound is 4-amino-1-(4-methoxybenzyl)-1H-imidazo[4,5-c]quinolin-2-ol, or a pharmaceutically acceptable salt thereof.
18. A pharmaceutical composition comprising a therapeutically effective amount of a compound or salt of claim 1 and a pharmaceutically acceptable carrier.
19. A method of inducing cytokine biosynthesis in an animal comprising administering an effective amount of a compound or salt of claim 1 to the animal.
20. A method of selectively inducing the biosynthesis of IFN-α in an animal comprising administering an effective amount of a compound or salt of claim 1 to the animal.
21. The compound or salt of claim 1 wherein the compound is 4-amino-1-[(1R)-1-phenylethyl]-1H-imidazo[4,5-c]quinolin-2-ol, or a pharmaceutically acceptable salt thereof.
22. The compound or salt of claim 1 wherein the compound is 4-amino-1-[(1S)-1-phenylethyl]-1H-imidazo[4,5-c]quinolin-2-ol, or a pharmaceutically acceptable salt thereof.

* * * * *

UNITED STATES PATENT AND TRADEMARK OFFICE
CERTIFICATE OF CORRECTION

PATENT NO.       : 8,377,957 B2                              Page 1 of 4
APPLICATION NO.  : 13/306366
DATED            : February 19, 2013
INVENTOR(S)      : Tushar Ashok Kshirsagar et al.

It is certified that error appears in the above-identified patent and that said Letters Patent is hereby corrected as shown below:

On the Title Page

Page 2, Column 2
Line 12, Delete "Stroermer et al." and
insert - - Stoermer et al. - -, therefor.

Page 3, Column 2
Line 30, Delete ""Cyctokine " and
insert - - "Cytokine - -, therefor.

Specification

Column 1
Line 8, Delete "file" and
insert - - filed - -, therefor.

Column 4
Line 12, Delete "Z—X—Y—X—Y—R$_4$," and
insert - - —Z—X—Y—X—Y—R$_4$, - -, therefor.

Column 5
Line 33, Delete "—N(-Q-R$_4$—," and
insert - - —N(-Q-R$_4$)—, - -, therefor.

Signed and Sealed this
Sixth Day of August, 2013

Teresa Stanek Rea
*Acting Director of the United States Patent and Trademark Office*

CERTIFICATE OF CORRECTION (continued)
U.S. Pat. No. 8,377,957 B2

Column 7
Line 5, Delete "Z—X—Y—X—Y—R$_4$," and
insert - - —Z—X—Y—X—Y—R$_4$, - -, therefor.

Column 8
Line 24, Delete "—N(-Q-R$_4$—," and
insert - - —N(-Q-R$_4$)—, - -, therefor.

Column 8
Line 56, Delete "—R;" and
insert - - —R'; - -, therefor.

Column 9
Line 52, Delete "Z—X—Y—X—Y—R$_4$," and
insert - - —Z—X—Y—X—Y—R$_4$, - -, therefor.

Column 11
Line 4, Delete "—N(-Q-R$_4$—," and
insert - - —N(-Q-R$_4$)—, - -, therefor.

Column 12
Line 62-63, Delete "arylalkylenyl" and
insert - - arylalkylenyl; - -, therefor.

Column 14
Line 4, Delete "Z—X—Y—X—Y—R$_4$," and
insert - - —Z—X—Y—X—Y—R$_4$, - -, therefor.

Column 15
Line 48, Delete "R$_H$" and
insert - - R$_{11}$ - -, therefor.

Column 15
Line 50, Delete "R$_H$" and
insert - - R$_{11}$ - -, therefor.

Column 15
Line 51, Delete "R$_H$" and
insert - - R$_{11}$ - -, therefor.

Column 17
Line 11, Delete "alkylene" and
insert - - alkylene. - -, therefor.

Column 22
Lines 19-28, Delete "The need for such protection will vary ................John Wiley & Sons, New York, USA, 1991." and
insert the same on Col. 22, Line 18, after "intermediate" as a continuation of the Paragraph.

CERTIFICATE OF CORRECTION (continued)
U.S. Pat. No. 8,377,957 B2

Column 23
Line 5, Delete "Ito" and
insert -- I to --, therefor.

Column 27
Line 5, Delete "in of" and
insert -- above in --, therefor.

Column 27
Line 9, Delete "of is" and
insert -- is --, therefor.

Column 28
Line 12, Delete "a the" and
insert -- the --, therefor.

Column 29
Line 14, Delete "animate" and
insert -- aminate --, therefor.

Column 29
Line 22, Delete "$S(O)_2)_{2-0}$," and
insert -- $S(O)_2)_2O$, --, therefor.

Column 30
Line 29, Delete "hydroylizable" and
insert -- hydrolyzable --, therefor.

Column 30
Line 65, Delete "Cl_6" and
insert -- $C_{1-6}$- --, therefor.

Column 33
Lines 54-55, Delete "carnii" and
insert -- carinii --, therefor.

Column 33
Line 61, Delete "myelogeous" and
insert -- myelogenous --, therefor.

Column 33
Line 67, Delete "Ommen's" and
insert -- Omenn's --, therefor.

Column 34
Line 2, Delete "thrombocythaemia," and
insert -- thrombocythemia, --, therefor.

CERTIFICATE OF CORRECTION (continued)
U.S. Pat. No. 8,377,957 B2

Column 34
Line 3, Delete "greata;" and
insert -- areata; --, therefor.

Column 34
Line 21, Delete "hemophilus" and
insert -- haemophilus --, therefor.

Column 37
Line 39, Delete "filtration washed" and
insert -- filtration and washed --, therefor.

Column 41
Lines 5-6, Delete "1402. Found" and
insert -- 1402, found --, therefor.

Column 43
Line 32, Delete "amine" and
insert -- amine. --, therefor.

Column 44
Line 30, Delete "3-[4-chloro" and
insert -- 3-[(4-chloro --, therefor.

Column 79 (table)
Line 10, Delete "Methyls" and
insert -- Methyl --, therefor.

Column 85
Line 23, Delete "$R_{1a}$ substituent" and
insert -- $R_{3a}$ substituent --, therefor.

Column 86
Line 10, Delete "et." and
insert -- et --, therefor.